US006204061B1

(12) United States Patent
Capecchi et al.

(10) Patent No.: US 6,204,061 B1
(45) Date of Patent: *Mar. 20, 2001

(54) CELLS AND NON-HUMAN ORGANISMS CONTAINING PREDETERMINED GENOMIC MODIFICATIONS AND POSITIVE-NEGATIVE SELECTION METHODS AND VECTORS FOR MAKING SAME

(75) Inventors: Mario R. Capecchi; Kirk R. Thomas, both of Salt Lake City, UT (US)

(73) Assignee: University of Utah Research Foundation, Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/781,559

(22) Filed: Jan. 9, 1997

Related U.S. Application Data

(60) Continuation of application No. 08/461,827, filed on Jun. 5, 1995, now Pat. No. 5,627,059, which is a division of application No. 08/014,083, filed on Feb. 4, 1993, now Pat. No. 5,464,764, which is a continuation of application No. 08/084,741, filed on Jun. 28, 1993, now Pat. No. 5,487,992, which is a continuation of application No. 07/397,707, filed on Aug. 22, 1989, now abandoned.

(51) Int. Cl.[7] ........................... C12N 15/87; C12N 15/63; C12N 15/00; C12N 5/00
(52) U.S. Cl. ..................... 435/463; 435/320.1; 435/325; 435/352; 435/354; 435/363; 435/455
(58) Field of Search .......................... 800/2, DIG. 1; 435/172.3, 325, 352, 354, 363, 320.1, 455, 463

(56) References Cited

U.S. PATENT DOCUMENTS

| 5,413,923 | * | 5/1995 | Kucherlapati et al. | 435/463 |
|---|---|---|---|---|
| 5,416,260 | * | 5/1995 | Koller et al. | 800/11 |
| 5,464,764 | * | 11/1995 | Capecchi et al. | 435/325 |
| 5,487,992 | * | 1/1996 | Capecchi et al. | 435/6 |
| 5,627,059 | * | 5/1997 | Capecchi et al. | 800/21 |
| 5,650,550 | * | 7/1997 | Korach et al. | 800/9 |
| 5,849,989 | * | 12/1998 | Edlund | 800/9 |

OTHER PUBLICATIONS

RA Hock et al (1986) Nature 320: 275–277.*
HS Kim et al (1988) Nucleic Acids Research 16: 8887–8903.*
Buttin (1987) Trends in Genetics 3: 205–206.*
LM Houdebine (1994) J Biotechnology 34: 269–287.*
A Gossler et al (1986) Proc Natl Acad Sci USA 83: 9065–9069.*
AL Joyner et al (1989) Nature 338: 158–155.*
KR Thomas et al (1987) Cell 51: 503–512.*
RK Saiki et al (1988) Science 239: 487–491.*
SL Mansour et al (1988) Nature 336: 348–352.*
MR Capecchi (1989) Trends in Genetics 5: 70–76.*
MR Capecchi (1989) Science 244: 1288–1292.*

* cited by examiner

*Primary Examiner*—Bruce R. Campell
*Assistant Examiner*—Ann-Marie Baker
(74) *Attorney, Agent, or Firm*—Townsend and Townsend and Crew LLP

(57) ABSTRACT

Positive-negative selector (PNS) vectors are provided for modifying a target DNA sequence contained in the genome of a target cell capable of homologous recombination. The vector comprises a first DNA sequence which contains at least one sequence portion which is substantially homologous to a portion of a first region of a target DNA sequence. The vector also includes a second DNA sequence containing at least one sequence portion which is substantially homologous to another portion of a second region of a target DNA sequence. A third DNA sequence is positioned between the first and second DNA sequences and encodes a positive selection marker which when expressed is functional in the target cell in which the vector is used. A fourth DNA sequence encoding a negative selection marker, also functional in the target cell, is positioned 5' to the first or 3' to the second DNA sequence and is substantially incapable of homologous recombination with the target DNA sequence. The invention also includes transformed cells containing at least one predetermined modification of a target DNA sequence contained in the genome of the cell. In addition, the invention includes organisms such as non-human transgenic animals and plants which contain cells having predetermined modifications of a target DNA sequence in the genome of the organism.

7 Claims, 13 Drawing Sheets

CELLS AND NON-HUMAN ORGANISMS CONTAINING PREDETERMINED GENOMIC MODIFICATIONS AND POSITIVE-NEGATIVE SELECTION METHODS AND VECTORS FOR MAKING SAME

CROSS-REFERENCE TO RELATED APPLICATIONS

This is a Continuation application Ser. No. 08/461,827, filed on Jun. 5, 1995, now U.S. Pat. No. 5,627,059, the disclosure of which is incorporated by reference.

This application is a 37 CFR §1.53 divisional application of commonly-owned, application Ser. No. 08/014,083, filed Feb. 4, 1993, now U.S. Pat. No. 5,464,764, which is a continuation of Ser. No. 08/084,741, Jun. 28, 1993, now U.S. Pat. No. 5,487,992, which is a continuation of Ser. No. 07/397,707, filed Aug. 22, 1989, now abandoned. These documents are hereby incorporated by reference for all purposes.

TECHNICAL FIELD OF THE INVENTION

The invention relates to cells and non-human organisms containing predetermined genomic modifications of the genetic material contained in such cells and organisms. The invention also relates to methods and vectors for making such modifications.

BACKGROUND OF THE INVENTION

Many unicellular and multicellular organisms have been made containing genetic material which is not otherwise normally found in the cell or organism. For example, bacteria, such as *E. coli*, have been transformed with plasmids which encode heterologous polypeptides, i.e., polypeptides not normally associated with that bacterium. Such transformed cells are routinely used to express the heterologous gene to obtain the heterologous polypeptide. Yeasts, filamentous fungi and animal cells have also been transformed with genes encoding heterologous polypeptides. In the case of bacteria, heterologous genes are readily maintained by way of an extra chromosomal element such as a plasmid. More complex cells and organisms such as filamentous fungi, yeast and mammalian cells typically maintain the heterologous DNA by way of integration of the foreign DNA into the genome of the cell or organism. In the case of mammalian cells and most multicellular organisms such integration is most frequently random within the genome.

Transgenic animals containing heterologous genes have also been made. For example, U.S. Pat. No. 4,736,866 discloses transgenic non-human mammals containing activated oncogenes. Other reports for producing transgenic animals include PTC Publication No. W082/04443 (rabbit β-globin gene DNA fragment injected into the pronucleus of a mouse zygote); EPO Publication No. 0 264 166 (Hepatitis B surface antigen and tPA genes under control of the whey acid protein promotor for mammary tissue specific expression); EPO Publication No. 0 247 494 (transgenic mice containing heterologous genes encoding various forms of insulin); PTC Publication No. W088/00239 (tissue specific expression of a transgene encoding factor IX under control of a whey protein promoter); PTC Publication No. W088/01648 (transgenic mammal having mammary secretory cells incorporating a recombinant expression system comprising a mammary lactogen-inducible regulatory region and a structural region encoding a heterologous protein); and EPO Publication No. 0 279 582 (tissue specific expression of chloramphenicol acetyltrans-ferase under control of rat β-casein promoter in transgenic mice). The methods and DNA constructs ("transgenes") used in making these transgenic animals also result in the random integration of all or part of the transgene into the genome of the organism. Typically, such integration occurs in an early embryonic stage of development which results in a mosaic transgenic animal. Subsequent generations can be obtained, however, wherein the randomly inserted transgene is contained in all of the somatic cells of the transgenic animals.

Transgenic plants have also been produced. For example, U.S. Pat. No. 4,801,540 to Hiatt, et al., discloses the transformation of plant cells with a plant expression vector containing tomato polygalacturonase (PG) oriented in the opposite orientation for expression. The anti-sense RNA expressed from this gene is capable of hybridizing with endogenous PG mRNA to suppress translation. This inhibits production of PG and as a consequence the hydrolysis of pectin by PG in the tomato.

While the integration of heterologous DNA into cells and organisms is potentially useful to produce transformed cells and organisms which are capable of expressing desired genes and/or polypeptides, many problems are associated with such systems. A major problem resides in the random pattern of integration of the heterologous gene into the genome of cells derived from multicellular organisms such as mammalian cells. This often results in a wide variation in the level of expression of such heterologous genes among different transformed cells. Further, random integration of heterologous DNA into the genome may disrupt endogenous genes which are necessary for the maturation, differentiation and/or viability of the cells or organism. In the case of transgenic animals, gross abnormalities are often caused by random integration of the transgene and gross rearrangements of the transgene and/or endogenous DNA often occur at the insertion site. For example, a common problem associated with transgenes designed for tissue-specific expression involves the "leakage" of expression of the transgenes. Thus, transgenes designed for the expression and secretion of a heterologous polypeptide in mammary secretory cells may also be expressed in brain tissue thereby producing adverse effects in the transgenic animal. While the reasons for transgene "leakage" and gross rearrangements of heterologous and endogenous DNA are not known with certainty, random integration is a potential cause of expression leakage.

One approach to overcome problems associated with random integration involves the use gene of targeting. This method involves the selection for homologous recombination events between DNA sequences residing in the genome of a cell or organism and newly introduced DNA sequences. This provides means for systematically altering the genome of the cell or organism.

For example, Hinnen, J. B., et al. (1978) *Proc. Natl. Acad. Sci. U.S.A.*, 75, 1929–1933 report homologous recombination between a leu2+ plasmid and a leu2⁻ gene in the yeast genome. Successful homologous transformants were positively selected by growth on media deficient in leucine.

For mammalian systems, several laboratories have reported the insertion of exogenous DNA sequences into specific sites within the mammalian genome by way of homologous recombination. For example, Smithies, O., et al. (1985) *Nature*, 317, 230–234 report the insertion of a linearized plasmid into the genome of cultured mammalian cells near the β-globin gene by homologous recombination.

The modified locus so obtained contained inserted vector sequences containing a neomycin resistance gene and a sup F gene encoding an amber suppressor t-RNA positioned between the δ and β-globin structural genes. The homologous insertion of this vector also resulted in the duplication of some of the DNA sequence between the δ and β-globin genes and part of the β-globin gene itself. Successful transformants were selected using a neomycin related antibiotic. Since most transformation events randomly inserted this plasmid, insertion of this plasmid by homologous recombination did not confer a selectable, cellular phenotype for homologous recombination mediated transformation. A laborious screening test for identifying predicted targeting events using plasmid rescue of the supF marker in a phage library prepared from pools of transfected colonies was used. Sib selection utilizing this assay identified the transformed cells in which homologous recombination had occurred.

A significant problem encountered in detecting and isolating cells, such as mammalian and plant cells, wherein homologous recombination events have occurred lies in the greater propensity for such cells to mediate non-homologous recombination. See Roth, D. B., et al. (1985) *Proc. Natl. Acad. Sci. U.S.A.,* 82 3355–3359; Roth, D. B., et al. (1985), *Mol. Cell. Biol.,* 5 2599–2607; and Paszkowski, J., et al. (1988), *EMBO J.,* 7, 4021–4026. In order to identify homologous recombination events among the vast pool of random insertions generated by non-homologous recombination, early gene targeting experiments in mammalian cells were designed using cell lines carrying a mutated form of either a neomycin resistance ($neo^r$) gene or a herpes simplex virus thymidine kinase (HSV-tk) gene, integrated randomly into the host genome. Such exogenous defective genes were then specifically repaired by homologous recombination with newly introduced exogenous DNA carrying the same gene bearing a different mutation. Productive gene targeting events were identified by selection for cells with the wild type phenotype, either by resistance to the drug G418 ($neo^r$) or ability to grow in HAT medium ($tk^+$). See, e.g., Folger, K. R., et al. (1984), *Cold Spring Harbor Symp. Quant. Biol.,* 49, 123–138; Lin, F. L. et al. (1984), *Cold Spring Harbor Symp. Quant. Biol.,* 49, 139–149; Smithies, O., et al. (1984), *Cold Spring Harbor Symp. Quant. Biol.,* 49, 161–170; Smith, A. J. H., et al. (1984), *Cold Spring Harbor Symp. Quant. Biol.,* 49, 171–181; Thomas K. R., et al. (1986), *Cell,* 41, 419–428; Thomas, K. R., et al. (1986), *Nature,* 324, 34–38; Doetschman, T., et al. (1987), *Nature,* 330, 576–578; and Song, Kuy-Young, et al. (1987), *Proc. Natl. Acad. Sci. U.S.A.,* 84, 6820–6824. A similar approach has been used in plant cells where partially deleted neomycin resistance genes reportedly were randomly inserted into the genome of tobacco plants. Transformation with vectors containing the deleted sequences conferred resistance to neomycin in those plant cells wherein homologous recombination occurred. Paszkowski, J., et al. (1988), *EMBO J.,* 7, 4021–4026.

A specific requirement and significant limitation to this approach is the necessity that the targeted gene confer a positive selection characteristic in those cells wherein homologous recombination has occurred. In each of the above cases, a defective exogenous positive selection marker was inserted into the genome. Such a requirement severely limits the utility of such systems to the detection of homologous recombination events involving inserted selectable genes.

In a related approach, Thomas, K. R., et al. (1987), *Cell,* 51, 503–512, report the disruption of a selectable endogenous mouse gene by homologous recombination. In this approach, a vector was constructed containing a neomycin resistance gene inserted into sequences encoding an exon of the mouse hypoxanthine phosphoribosyl transferase (Hprt) gene. This endogenous gene was selected for two reasons. First, the Hprt gene lies on the X-chromosome. Since embryonic stem cells (ES cells) derived from male embryos are hemizygous for Hprt, only a single copy of the Hprt gene need be inactivated by homologous recombination to produce a selectable phenotype. Second, selection procedures are available for isolating Hprt⁻ mutants. Cells wherein homologous recombination events occurred could thereafter be positively selected by detecting cells resistant to neomycin ($neo^R$) and 6-thioguanine (Hprt⁻).

A major limitation in the above methods has been the requirement that the target sequence in the genome, either endogenous or exogenous, confer a selection characteristic to the cells in which homologous recombination has occurred (i.e. $neo^R$, $tk^+$ or Hprt⁻). Further, for those gene sequences which confer a selectable phenotype upon homologous recombination (e.g. the Hprt gene), the formation of such a selectable phenotype requires the disruption of the endogenous gene.

The foregoing approaches to gene targeting are clearly not applicable to many emerging technologies. See, e.g. Friedman, T. (1989), *Science,* 244, 1275–1281 (human gene therapy); Gasser, C. S., et al., Id., 1293–1299 (genetic engineering of plants); Pursel, I. G., et al., Id. 1281–1288 (genetic engineering of livestock); and Timberlake, W. E., et al., Id. et al., 13-13, 1312 (genetic engineering of filamentous fungi). Such techniques are generally not useful to isolate transformants wherein non-selectable endogenous genes are disrupted or modified by homologous recombination. The above methods are also of little or no use for gene therapy because of the difficulty in selecting cells wherein the genetic defect has been corrected by way of homologous recombination.

Recently, several laboratories have reported the expression of an expression-defective exogenous selection marker after homologous integration into the genome of mammalian cells. Sedivy, J. M., et al. (1989), *Proc. Nat. Acad. Sci. U.S.A.,* 86, 227–231, report targeted disruption of the hemizygous polyomavirus middle-T antigen with a neomycin resistance gene lacking an initiation codon. Successful transformants were selected for resistance to G418. Jasin, M., et al. (1988), *Genes and Development,* 2, 1353–1363 report integration of an expression-defective gpt gene lacking the enhancer in its SV40 early promotor into the SV40 early region of a gene already integrated into the mammalian genome. Upon homologous recombination, the defective gpt gene acts as a selectable marker.

Assays for detecting homologous recombination have also recently been reported by several laboratories. Kim, H. S., et al. (1988), *Nucl. Acid. S. Res.,* 16, 8887–8903, report the use of the polymerase chain reaction (PCR) to identify the disruption of the mouse hprt gene. A similar strategy has been used by others to identify the disruption of the Hox 1.1 gene in mouse ES cells (Zimmmer, A. P., et al. (1989), *Nature,* 338, 150–153) and the disruption of the En-2 gene by homologous recombination in embryonic stem cells. (Joyner, A. L., et al. (1989), *Nature,* 338, 153–156).

It is an object herein to provide methods whereby any predetermined region of the genome of a cell or organism may be modified and wherein such modified cells can be selected and enriched.

It is a further object of the invention to provide novel vectors used in practicing the above methods of the invention.

Still further, an object of the invention is to provide transformed cells which have been modified by the methods and vectors of the invention to contain desired mutations in specific regions of the genome of the cell.

Further, it is an object herein to provide non-human transgenic organisms, which contain cells having predetermined genomic modifications.

The references discussed above are provided solely for their disclosure prior to the filing date of the present application. Nothing herein is to be construed as an admission that the inventors are not entitled to antedate such disclosure by virtue of prior invention.

SUMMARY OF THE INVENTION

In accordance with the above objects, positive-negative selector (PNS) vectors are provided for modifying a target DNA sequence contained in the genome of a target cell capable of homologous recombination. The vector comprises a first DNA sequence which contains at least one sequence portion which is substantially homologous to a portion of a first region of a target DNA sequence. The vector also includes a second DNA sequence containing at least one sequence portion which is substantially homologous to another portion of a second region of a target DNA sequence. A third DNA sequence is positioned between the first and second DNA sequences and encodes a positive selection marker which when expressed is functional in the target cell in which the vector is used. A fourth DNA sequence encoding a negative selection marker, also functional in the target cell, is positioned 5' to the first or 3' to the second DNA sequence and is substantially incapable of homologous recombination with the target DNA sequence.

The above PNS vector containing two homologous portions and a positive and a negative selection marker can be used in the methods of the invention to modify target DNA sequences. In this method, cells are first transfected with the above vector. During this transformation, the PNS vector is most frequently randomly integrated into the genome of the cell. In this case, substantially all of the PNS vector containing the first, second, third and fourth DNA sequences is inserted into the genome. However, some of the PNS vector is integrated into the genome via homologous recombination. When homologous recombination occurs between the homologous portions of the first and second DNA sequences of the PNS vector and the corresponding homologous portions of the endogenous target DNA of the cell, the fourth DNA sequence containing the negative selection marker is not incorporated into the genome. This is because the negative selection marker lies outside of the regions of homology in the endogenous target DNA sequence. As a consequence, at least two cell populations are formed. That cell population wherein random integration of the vector has occurred can be selected against by way of the negative selection marker contained in the fourth DNA sequence. This is because random events occur by integration at the ends of linear DNA. The other cell population wherein gene targeting has occurred by homologous recombination are positively selected by way of the positive selection marker contained in the third DNA sequence of the vector. This cell population does not contain the negative selection marker and thus survives the negative selection. The net effect of this positive-negative selection method is to substantially enrich for transformed cells containing a modified target DNA sequence.

If in the above PNS vector, the third DNA sequence containing the positive selection marker is positioned between first and second DNA sequences corresponding to DNA sequences encoding a portion of a polypeptide (e.g. within the exon of a eucaryotic organism) or within a regulatory region necessary for gene expression, homologous recombination allows for the selection of cells wherein the gene containing such target DNA sequences is modified such that it is non functional.

If, however, the positive selection marker contained in the third DNA sequence of the PNS vector is positioned within an untranslated region of the genome, e.g. within an intron in a eucaryotic gene, modifications of the surrounding target sequence (e.g. exons and/or regulatory regions) by way of substitution, insertion and/or deletion of one or more nucleotides may be made without eliminating the functional character of the target gene.

The invention also includes transformed cells containing at least one predetermined modification of a target DNA sequence contained in the genome of the cell.

In addition, the invention includes organisms such as non-human transgenic animals and plants which contain cells having predetermined modifications of a target DNA sequence in the genome of the organism.

Various other aspects of the invention will be apparent from the following detailed description, appended drawings and claims.

DETAILED DESCRIPTION OF THE INVENTION

The positive-negative selection ("PNS") methods and vectors of the invention are used to modify target DNA sequences in the genome of cells capable of homologous recombination.

Figure 1:
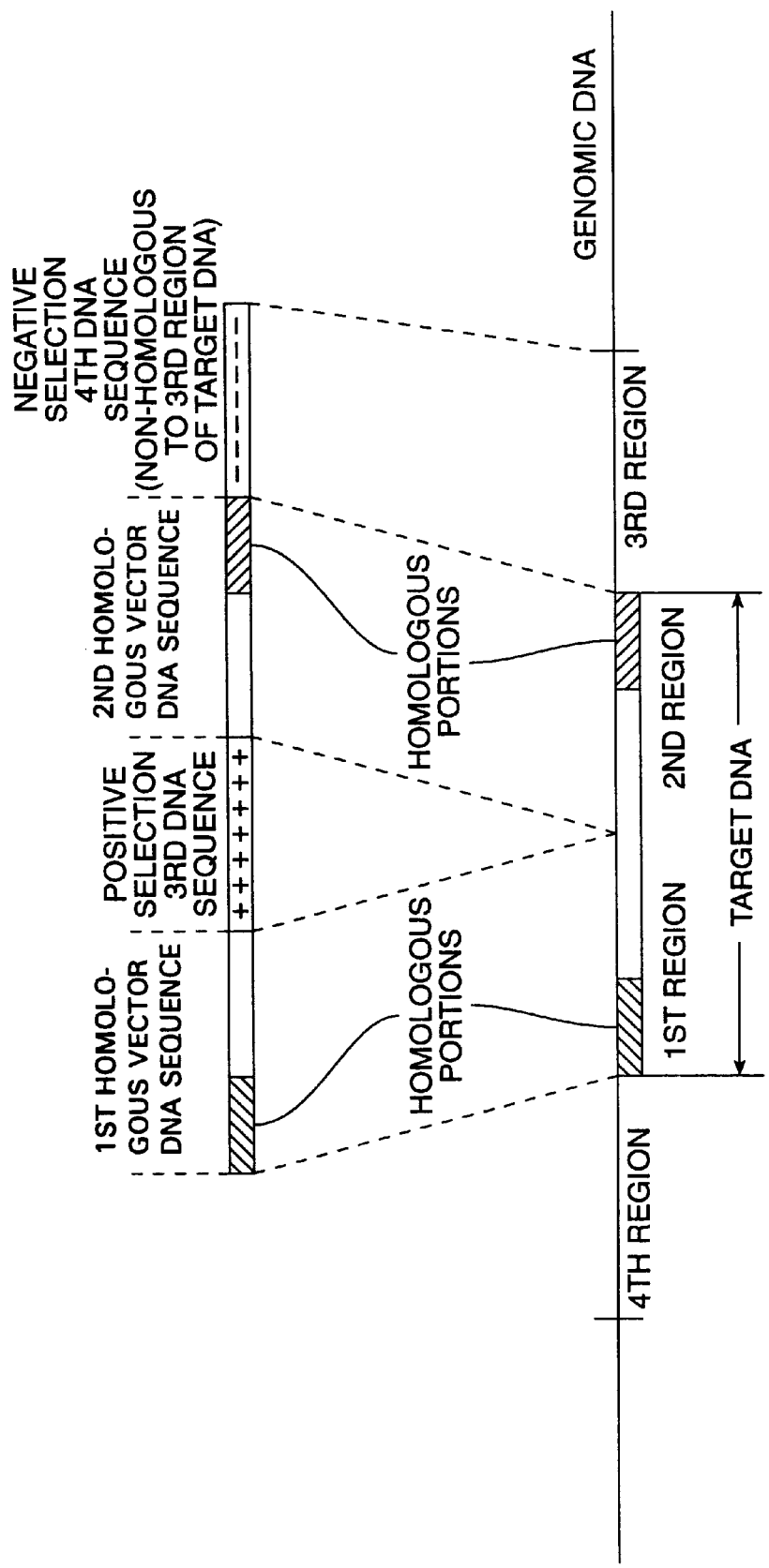
FIG. 1 depicts the positive-negative selection (PNS) vector of the invention and a target DNA sequence.

A schematic diagram of a PNS vector of the invention is shown in FIG. 1. As can be seen, the PNS vector comprises four DNA sequences. The first and second DNA sequences each contain portions which are substantially homologous to corresponding homologous portions in first and second regions of the targeted DNA. Substantial homology is necessary between these portions in the PNS vector and the target DNA to insure targeting of the PNS vector to the appropriate region of the genome.

As used herein, a "target DNA sequence" is a predetermined region within the genome of a cell which is targeted for modification by the PNS vectors of the invention. Target DNA sequences include structural genes (i.e., DNA sequences encoding polypeptides including in the case of eucaryots, introns and exons), regulatory sequences such as enhancers sequences, promoters and the like and other regions within the genome of interest. A target DNA sequence may also be a sequence which, when targeted by a vector has no effect on the function of the host genome. Generally, the target DNA contains at least first and second regions. See FIG. 1. Each region contains a homologous sequence portion which is used to design the PNS vector of the invention. In some instances, the target DNA sequence also includes a third and in some cases a third and fourth region. The third and fourth regions are substantially contiguous with the homologous portions of the first and second region. The homologous portions of the target DNA are homologous to sequence portions contained in the PNS vector. The third and in some cases third and fourth regions define genomic DNA sequences within the target DNA sequence which are not substantially homologous to the fourth and in some cases fourth and fifth DNA sequences of the PNS vector.

Also included in the PNS vector are third and fourth DNA sequences which encode respectively "positive" and "negative" selection markers. Examples of preferred positive and negative selection markers are listed in Table I. The third DNA sequence encoding the positive selection marker is positioned between the first and second DNA sequences while the fourth DNA sequence encoding the negative selection marker is positioned either 3' to the second DNA sequences shown in FIG. 1, or 5' to the first DNA sequence (not shown in FIG. 1). The positive and negative selection markers are chosen such that they are functional in the cells containing the target DNA.

Positive and/or negative selection markers are "functional" in transformed cells if the phenotype expressed by the DNA sequences encoding such selection markers is capable of conferring either a positive or negative selection characteristic for the cell expressing that DNA sequence. Thus, "positive selection" comprises contacting cells transfected with a PNS vector with an appropriate agent which kills or otherwise selects against cells not containing an integrated positive selection marker. "Negative selection" on the other hand comprises contacting cells transfected with the PNS vector with an appropriate agent which kills or otherwise selects against cells containing the negative selection marker. Appropriate agents for use with specific positive and negative selection markers and appropriate concentrations are listed in Table I. Other positive selection markers include DNA sequences encoding membrane bound polypeptides. Such polypeptides are well known to those skilled in the art and contain a secretory sequence, an extracellular domain, a transmembrane domain and an intracellular domain. When expressed as a positive selection marker, such polypeptides associate with the target cell membrane. Fluorescently labelled antibodies specific for the extracellular domain may then be used in a fluoresence activated cell sorter (FACS) to select for cells expressing the membrane bound polypeptide. FACS selection may occur before or after negative selection.

TABLE I

Selectable Markers for Use in PNS-Vectors

| Gene | Type | Selective Agents | Preferred Concentration of selective Agent | Organism |
|---|---|---|---|---|
| Neo | + | G418 | 50–1000 µg/ml | Eukaryotes |
| Neo | + | Kanamycin | 5–500 µg/ml | Plants |
| Hyg | + | Hygromycin | 10–1000 µg/ml | Eukaryotes |
| hisD | + | Histidinol | 5–500 µg/ml | Animals |
| Gpt | + | Xanthine, | 50–500 µg/ml | Animals |
| Ble | + | Bleomycin | 1–100 µg/ml | Plants |
| Hprt | + | Hypoxanthine | 0.01–10 mM | All |
| HSV-tk | – | Acyclovir | 1–100 µM | Animals |
|  |  | Gancyclovir | 0.05–200 µM | Animals |
|  |  | FIAU | 0.02–100 µM | Animals |
| Hprt | – | 6-thioguanine | 0.1–100 µg/ml | All |
| Gpt | – | 6-thioxanthine | 0.1–100 µg/ml | Animals |
| Diphtheria toxin | – | None | None | Animals |
| Ricin toxin | – | None | None | Animals |
| cytosine deaminase | – | 5-fluoro-cytosine | 10–500 µg/ml | All |

The expression of the negative selection marker in the fourth DNA sequence is generally under control of appropriate regulatory sequences which render its expression in the target cell independent of the expression of other sequences in the PNS vector or the target DNA. The positive selection marker in the third DNA, however, may be constructed so that it is independently expressed (eg. when contained in an intron of the target DNA) or constructed so that homologous recombination will place it under control of regulatory sequences in the target DNA sequence. The strategy and details of the expression of the positive selection marker will be discussed in more detail hereinafter.

The positioning of the negative selection marker as being either "5'" or "3'" is to be understood as relating to the positioning of the negative selection marker relative to the 5' or 3' end of one of the strands of the double-stranded PNS vector. This should be apparent from FIG. 1. The positioning of the various DNA sequences within the PNS vector, however, does not require that each of the four DNA sequences be transcriptionally and translationally aligned on a single strand of the PNS vector. Thus, for example, the first and second DNA sequences may have a 5' to 3' orientation consistent with the 5' to 3' orientation of regions 1 and 2 in the target DNA sequence. When so aligned, the PNS vector is a "replacement PNS vector" upon homologous recombination the replacement PNS vector replaces the genomic DNA sequence between the homologous portions of the target DNA with the DNA sequences between the homologous portion of the first and second DNA sequences of the PNS vector. Sequence replacement vectors are preferred in practicing the invention. Alternatively, the homologous portions of the first and second DNA sequence in the PNS vector may be inverted relative to each other such that the homologous portion of DNA sequence 1 corresponds 5' to 3' with the homologous portion of region 1 of the target DNA sequence whereas the homologous portion of DNA sequence 2 in the PNS vector has an orientation which is 3' to 5' for the homologous portion of the second region of the second region of the target DNA sequence. This inverted orientation provides for and "insertion PNS vector". When an insertion PNS vector is homologously inserted into the target DNA sequence, the entire PNS vector is inserted into the target DNA sequence without replacing the homologous portions in the target DNA. The modified target DNA so obtained necessarily contains the duplication of at least those homologous portions of the target DNA which are contained in the PNS vector. Sequence replacement vectors and sequence insertion vectors utilizing a positive selection marker only are described by Thomas et al. (1987), *Cell,* 51, 503–512.

Similarly, the third and fourth DNA sequences may be transcriptionally inverted relative to each other and to the transcriptional orientation of the target DNA sequence. This is only the case, however, when expression of the positive and/or negative selection marker in the third and/or fourth DNA sequence respectively is independently controlled by appropriate regulatory sequences. When, for example a promoterless positive selection marker is used as a third DNA sequence such that its expression is to be placed under control of an endogenous regulatory region, such a vector requires that the positive selection marker be positioned so that it is in proper alignment (5' to 3' and proper reading frame) with the transcriptional orientation and sequence of the endogenous regulatory region.

Positive-negative selection requires that the fourth DNA sequence encoding the negative marker be substantially incapable of homologous recombination with the target DNA sequence. In particular, the fourth DNA sequence should be substantially non-homologous to a third region of the target DNA. When the fourth DNA sequence is positioned 3' to the second DNA sequence, the fourth DNA sequence is non-homologous to a third region of the target DNA which is adjacent to the second region of the target DNA. See FIG. 1. When the fourth DNA sequence is located 5' to the first DNA sequence, it is non-homologous to a fourth region of the target DNA sequence adjacent to the first region of the target DNA.

In some cases, the PNS vector of the invention may be constructed with a fifth DNA sequence also encoding a negative selection marker. In such cases, the fifth DNA sequence is positioned at the opposite end of the PNS vector to that containing the fourth DNA sequence. The fourth DNA sequence is substantially non-homologous to the third region of the target DNA and the fifth DNA sequence is substantially non-homologous to the fourth region of the target DNA. The negative selection markers contained in such a PNS vector may either be the same or different negative selection markers. When they are different such that they require the use of two different agents to select again cells containing such negative markers, such negative selection may be carried out sequentially or simultaneously with appropriate agents for the negative selection marker. The positioning of two negative selection markers at the 5' and 3' end of a PNS vector further enhances selection against target cells which have randomly integrated the PNS vector. This is because random integration sometimes results in the rearrangement of the PNS vector resulting in excision of all or part of the negative selection marker prior to random integration. When this occurs, cells randomly integrating the PNS vector cannot be selected against. However, the presence of a second negative selection marker on the PNS vector substantially enhances the likelihood that random integration will result in the insertion of at least one of the two negative selection markers.

The substantial non-homology between the fourth DNA sequence (and in some cases fourth and fifth DNA sequences) of the PNS vector and the target DNA creates a discontinuity in sequence homology at or near the juncture of the fourth DNA sequence. Thus, when the vector is integrated into the genome by way of the homologous recombination mechanism of the cell, the negative selection marker in the fourth DNA sequence is not transferred into the target DNA. It is the non-integration of this negative selection marker during homologous recombination which forms the basis of the PNS method of the invention.

As used herein, a "modifying DNA sequence" is a DNA sequence contained in the first, second and/or third DNA sequence which encodes the substitution, insertion and/or deletion of one or more nucleotides in the target DNA sequence after homologous insertion of the PNS vector into the targeted region of the genome. When the PNS vector contains only the insertion of the third DNA sequence encoding the positive selection marker, the third DNA sequence is sometimes referred to as a "first modifying DNA sequence". When in addition to the third DNA sequence, the PNS vector also encodes the further substitution, insertion and/or deletion of one or more nucleotides, that portion encoding such further modification is sometimes referred to as a "second modifying DNA sequence". The second modifying DNA sequence may comprise the entire first and/or second DNA sequence or in some instances may comprise less than the entire first and/or second DNA sequence. The latter case typically arises when, for example, a heterologous gene is incorporated into a PNS vector which is designed to place that heterologous gene under the regulatory control of endogenous regulatory sequences. In such a case, the homologous portion of, for example, the first DNA sequence may comprise all or part of the targeted endogenous regulatory sequence and the modifying DNA sequence comprises that portion of the first DNA sequence (and in some cases a part of the second DNA sequence as well) which encodes the heterologous DNA sequence. An appropriate homologous portion in the second DNA sequence will be included to complete the targeting of the PNS vector. On the other hand, the entire first and/or second DNA sequence may comprise a second modifying DNA sequence when, for example, either or both of these DNA sequences encode for the correction of a genetic defect in the targeted DNA sequence.

As used herein, "modified target DNA sequence" refers to a DNA sequence in the genome of a targeted cell which has been modified by a PNS vector. Modified DNA sequences contain the substitution, insertion and/or deletion of one or more nucleotides in a first transformed target cell as compared to the cells from which such transformed target cells are derived. In some cases, modified target DNA sequences are referred to as "first" and/or "second modified target DNA sequences". These correspond to the DNA sequence found in the transformed target cell when a PNS vector containing a first or second modifying sequence is homologously integrated into the target DNA sequence.

"Transformed target cells" sometimes referred to as "first transformed target cells" refers to those target cells wherein the PNS vector has been homologously integrated into the target cell genome. A "transformed cell" on the other hand refers to a cell wherein the PNS has non-homologously inserted into the genome randomly. "Transformed target cells" generally contain a positive selection marker within the modified target DNA sequence. When the object of the genomic modification is to disrupt the expression of a particular gene, the positive selection marker is generally contained within an exon which effectively disrupts transcription and/or translation of the targeted endogenous gene. When, however, the object of the genomic modification is to insert an exogenous gene or correct an endogenous gene defect, the modified target DNA sequence in the first transformed target cell will in addition contain exogenous DNA sequences or endogenous DNA sequences corresponding to those found in the normal, i.e., nondefective, endogenous gene.

"Second transformed target cells" refers to first transformed target cells whose genome has been subsequently modified in a predetermined way. For example, the positive selection marker contained in the genome of a first transformed target cell can be excised by homologous recombination to produce a second transformed target cell. The details of such a predetermined genomic manipulation will be described in more detail hereinafter.

As used herein, "heterologous DNA" refers to a DNA sequence which is different from that sequence comprising the target DNA sequence. Heterologous DNA differs from target DNA by the substitution, insertion and/or deletion of one or more nucleotides. Thus, an endogenous gene sequence may be incorporated into a PNS vector to target its insertion into a different regulatory region of the genome of the same organism. The modified DNA sequence so obtained is a heterologous DNA sequence. Heterologous DNA sequences also include endogenous sequences which have been modified to correct or introduce gene defects or to change the amino acid sequence encoded by the endogenous gene. Further, heterologous DNA sequences include exogenous DNA sequences which are not related to endogenous sequences, e.g. sequences derived from a different species. Such "exogenous DNA sequences" include those which encode exogenous polypeptides or exogenous regulatory sequences. For example, exogenous DNA sequences which can be introduced into murine or bovine ES cells for tissue specific expression (e.g. in mammary secretory cells) include human blood factors such as t-PA, Factor VIII, serum albumin and the like. DNA sequences encoding positive selection markers are further examples of heterologous DNA sequences.

The PNS vector is used in the PNS method to select for transformed target cells containing the positive selection marker and against those transformed cells containing the negative selection marker. Such positive-negative selection procedures substantially enrich for those transformed target cells wherein homologous recombination has occurred. As used herein, "substantial enrichment" refers to at least a two-fold enrichment of transformed target cells as compared to the ratio of homologous transformants versus nonhomologous transformants, preferably a 10-fold enrichment, more preferably a 1000-fold enrichment, most preferably a 10,000-fold enrichment, i.e., the ratio of transformed target cells to transformed cells. In some instances, the frequency of homologous recombination versus random integration is of the order of 1 in 1000 and in some cases as low as 1 in 10,000 transformed cells. The substantial enrichment obtained by the PNS vectors and methods of the invention often result in cell populations wherein about 1%, and more preferably about 20%, and most preferably about 95% of the resultant cell population contains transformed target cells wherein the PNS vector has been homologously integrated. Such substantially enriched transformed target cell populations may thereafter be used for subsequent genetic manipulation, for cell culture experiments or for the production of transgenic organisms such as transgenic animals or plants.

Figure 2A:
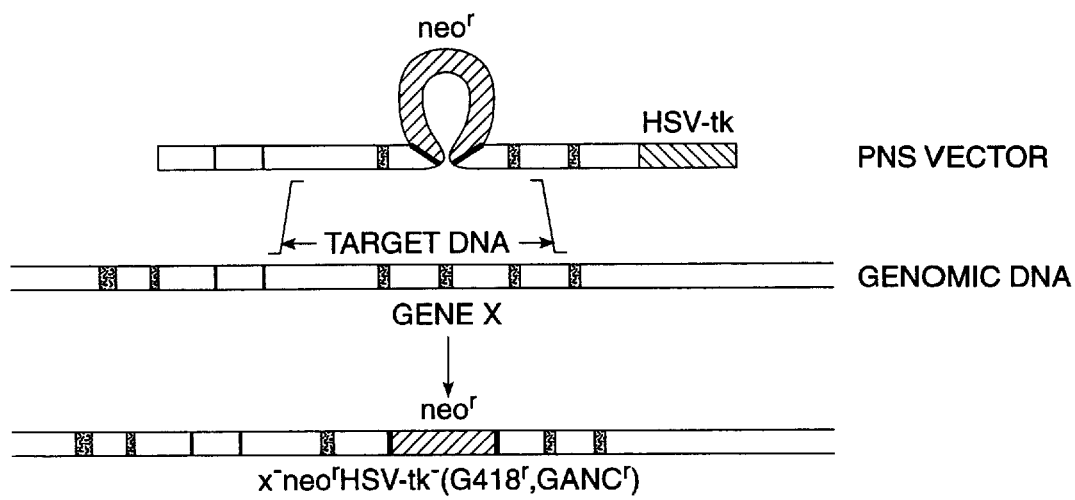
FIGS. 2a and 2b depict the results of gene targeting (homologous recombination) and random integration of a PNS vector into a genome.
Figure 2B:
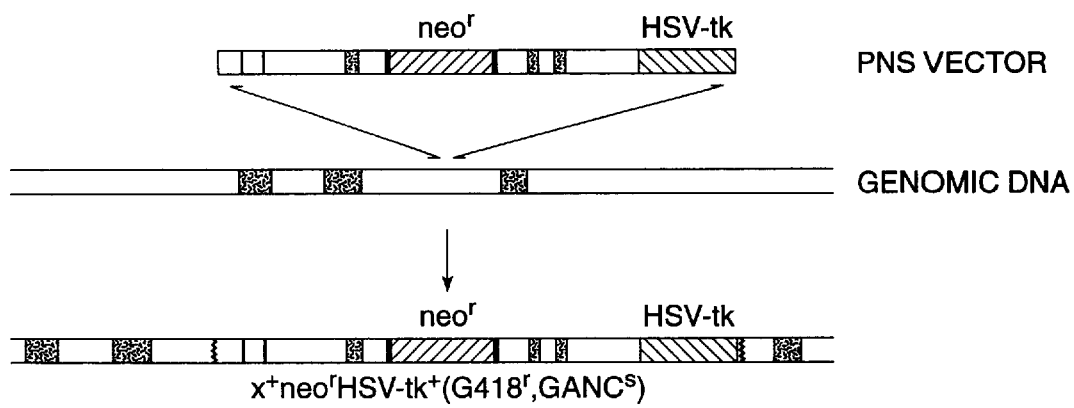

FIGS. 2a and 2b show the consequences of gene targeting (homologous recombination) and random integration of a PNS vector into the genome of a target cell. The PNS vector shown contains a neomycin resistance gene as a positive selection marker ($neo^r$) and a herpes simplex virus thymidine kinase (HSV-tk) gene as a negative selection marker. The $neo^r$ positive selection marker is positioned in an exon of gene X. This positive selection marker is constructed such that it's expression is under the independent control of appropriate regulatory sequences. Such regulatory sequences may be endogenous to the host cell in which case they are preferably derived from genes actively expressed in the cell type. Alteratively, such regulatory sequences may be inducible to permit selective activation of expression of the positive selection marker. on each side of the $neo^r$ marker are DNA sequences homologous to the regions 5' and 3' from the point of $neo^r$ insertion in the exon sequence. These flanking homologous sequences target the X gene for homologous recombination with the PNS vector. Consistent with the above description of the PNS vector, the negative selection marker HSV-tk is situated outside one of the regions of homology. In this example it is 3' to the transcribed region of gene X. The $neo^r$ gene confers resistance to the drug G418 ($G418^R$) whereas the presence of the HSV-tk gene renders cells containing this gene sensitive to gancyclovir ($GANC^s$). When the PNS vector is randomly inserted into the genome by a mechanism other than by homologous recombination (FIG. 2b), insertion is most frequently via the ends of the linear DNA and thus the phenotype for such cells is $neo^+$ $HSV-tk^+$ ($G418^R$, $GANC^s$). When the PNS vector is incorporated into the genome by homologous recombination as in FIG. 2a, the resultant phenotype is $neo^+$, HSV-tk-($G418^R$, $GANC^R$). Thus, those cells wherein random integration of the PNS vector has occurred can be selected against by treatment with GANC. Those remaining transformed target cells wherein homologous recombination has been successful can then be selected on the basis of neomycin resistance and GANC resistance. It, of course, should be apparent that the order of selection for and selection against a particular genotype is not important and that in some instances positive and negative selection can occur simultaneously.

As indicated, the neomycin resistance gene in FIG. 2 is incorporated into an exon of gene X. As so constructed, the integration of the PNS vector by way of homologous recombination effectively blocks the expression of gene X. In multicellular organisms, however, integration is predominantly random and occurs, for the most part, outside of the region of the genome encoding gene X. Non-homologous recombination therefore will not disrupt gene X in most instances. The resultant phenotypes will therefore, in addition to the foregoing, will also be $X^-$ for homologous recombination and $X^+$ for random integration. In many cases it is desirable to disrupt genes by positioning the positive selection marker in an exon of a gene to be disrupted or modified. For example, specific proto-oncogenes can be mutated by this method to produce transgenic animals. Such transgenic animals containing selectively inactivated proto-oncogenes are useful in dissecting the genetic contribution of such a gene to oncogenesis and in some cases normal development.

Another potential use for gene inactivation is disruption of proteinaceous receptors on cell surfaces. For example, cell lines or organisms wherein the expression of a putative viral receptor has been disrupted using an appropriate PNS vector can be assayed with virus to confirm that the receptor is, in fact, involved in viral infection. Further, appropriate PNS vectors may be used to produce transgenic animal models for specific genetic defects. For example, many gene defects have been characterized by the failure of specific genes to express functional gene product, e.g. a and p thalassema, hemophilia, Gaucher's disease and defects affecting the production of α-1-antitrypsin, ADA, PNP, phenylketonurea, familial hypercholesterolemia and retinoblastemia. Transgenic animals containing disruption of one or both alleles associated with such disease states or modification to encode the specific gene defect can be used as models for therapy. For those animals which are viable at birth, experimental therapy can be applied. When, however, the gene defect affects survival, an appropriate generation (e.g. F0, F1) of transgenic animal may be used to study in vivo techniques for gene therapy.

A modification of the foregoing means to disrupt gene X by way of homologous integration involves the use of a positive selection marker which is deficient in one or more regulatory sequences necessary for expression. The PNS vector is constructed so that part but not all of the regulatory sequences for gene X are contained in the PNS vector 5' from the structural gene segment encoding the positive selection marker, e.g., homologous sequences encoding part of the promotor of the X gene. As a consequence of this construction, the positive selection marker is not functional in the target cell until such time as it is homologously integrated into the promotor region of gene X. When so integrated, gene X is disrupted and such cells may be selected by way of the positive selection marker expressed under the control of the target gene promoter. The only limitation in using such an approach is the requirement that the targeted gene be actively expressed in the cell type used. Otherwise, the positive selection marker will not be expressed to confer a positive selection characteristic on the cell.

Figure 3:
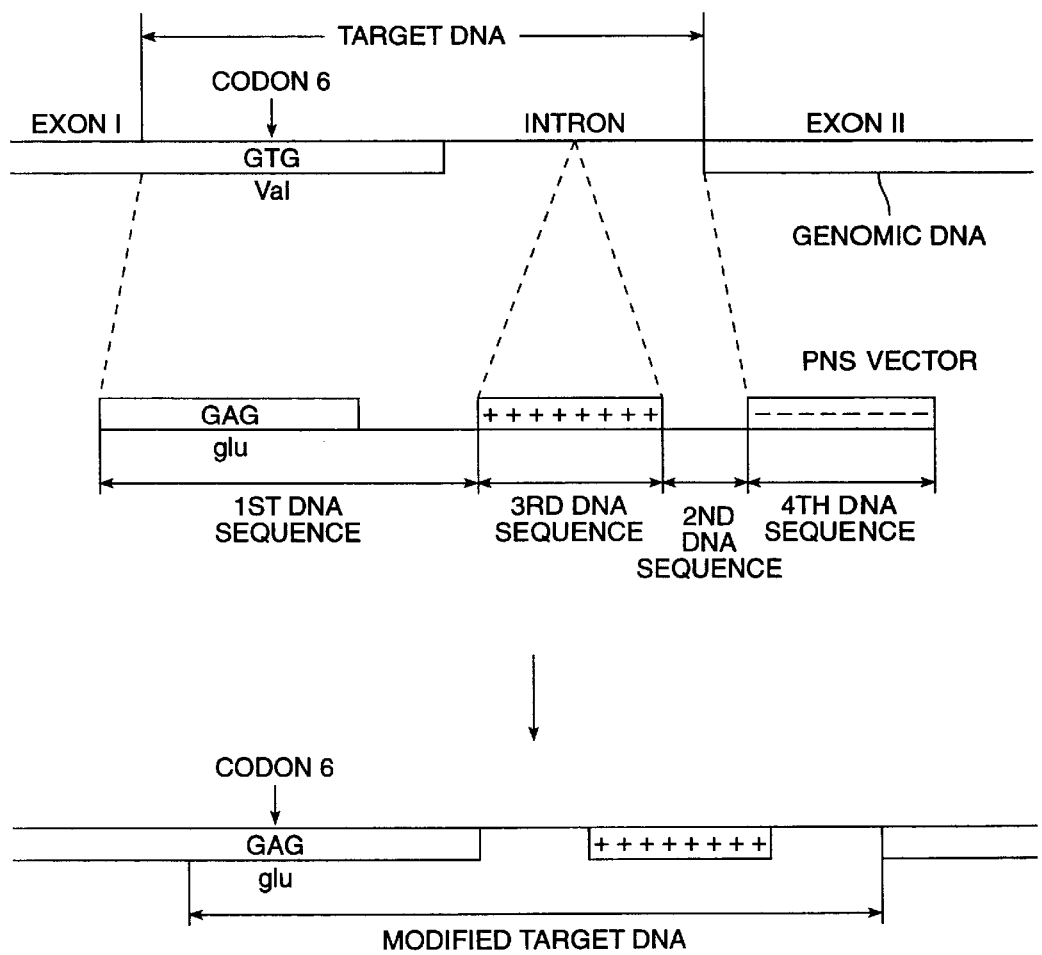
FIG. 3 depicts a PNS vector containing a positive selection marker within a sequence corresponding, in part, to an intron of a target DNA sequence.

In many instances, the disruption of an endogenous gene is undesirable, e.g., for some gene therapy applications. In such situations, the positive selection marker comprising the third DNA sequence of the PNS vector may be positioned within an untranslated sequence, e.g. an intron of the target DNA or 5' or 3' untranslated regions. FIG. 3 depicts such a PNS vector. As indicated, the first DNA sequence comprises part of exon I and a portion of a contiguous intron in the target DNA. The second DNA sequence encodes an adjacent portion of the same intron and optionally may include all or a portion of exon II. The positive selection marker of the third DNA sequence is positioned between the first and second sequences. The fourth DNA sequence encoding the negative selection marker, of course, is positioned outside of the region of homology. When the PNS vector is integrated into the target DNA by way of homologous recombination the positive selection marker is located in the intron of the targeted gene. The third DNA sequence is constructed such that it is capable of being expressed and translated independently of the targeted gene. Thus, it contains an independent functional promoter, translation initiation sequence, translation termination sequence, and in some cases a polyadenylation sequence and/or one or more enhancer sequences, each functional in the cell type transfected with the PNS vector. In this manner, cells incorporating the PNS vector by way of homologous recombination can be selected by way of the positive selection marker without disruption of the endogenous gene. Of course, the same regulatory sequences can be used to control the expression of the positive selection marker when it is positioned within an exon. Further, such regulatory sequences can be used to control expression of the negative selection marker. Regulatory sequences useful in controlling the expression of positive and/or negative selection markers are listed in Table IIB. Of course, other regulatory sequences may be used which are known to those skilled in the art. In each case, the regulatory sequences will be properly aligned and, if necessary, placed in proper reading frame with the particular DNA sequence to be expressed. Regulatory sequence, e.g. enhancers and promoters from different sources may be combined to provide modulated gene expression.

TABLE IIA

Tissue Specific Regulatory Sequences

| Cell/Tissue | Promoter/Enhancer | Reference |
|---|---|---|
| Adrenal | PNMT | Baetge, et al. (1988) PNAS 85 |
| Erythoroid | β-globin | Townes et al. (1985) EMBO J 4:1715 |
| Lens | α-crystallin | Overteek et al. (1985) PNAS 82:7815 |
| Liver | α-FP | Krumlauf et al. (1985) MCB 5:1639 |
| Lymphoid | IGµ (γ-1 promoter/enhancer | Yamamura et al. (1986) PNAS 83:2152 |
| Mammary | WAP | Gordon et al. (1987) Bio/Tech 5:1183 |
| Nervous | MBP | Tamura et al. (1989) MCB 9:3122 |
| Pancreas (B) | Insulin | Hanaban (1985) Nature 315:115 |
| Pancreas (exocrine) | Elastase | Swift et al. (1984) Cell 38:639 |
| Pituitary | Prolactin | Ingraham et al. (1988) Cell 55:579 |
| Skeletal Muscle | ckm | Johnson et al. (1989) MCB 9:3393 |
| Testes | Protamine | Stewart et al. (1988) MCB 8:1748 |

TABLE IIB

Regulatory Sequences for Use With Positive and/or Negative Selection Markers

| Regulatory Sequence | Cell Type |
|---|---|
| PYF441 enhancer/HSV-tk promoter (pMCI-Neo control) | embryo-derived |
| ASV-LTR | fibroblasts |
| SV-40 early | variety of mammalian cells |
| Cytomegalo virus | general mammalian |
| β-actin | general mammalian |
| MoMuLV | haemopoetic stem cells |
| SFFV | haemopoetic stem cells |
| Mannopine synthase | general plant |
| Octapine synthase | general plant |
| Nopaline synthase | general plant |
| Cauliflower mosiac virus 35S promoter/enhancer | general plant |
| β-phaseolin | seeds |
| "insert-7" | protoplasts |

A modification of the target DNA sequence is also shown in FIG. 3. In exon I of the target DNA sequence, the sixth codon GTG is shown which encodes valine. In the first DNA sequence of the PNS vector, the codon GAG replaces the GTG codon in exon I. This latter codon encodes glutamine. Cells selected for homologous recombination as a consequence encode a modified protein wherein the amino acid encoded by the sixth codon is changed from valine to glutamine.

There are, of course, numerous other examples of modifications of target DNA sequences in the genome of the cell which can be obtained by the PNS vectors and methods of the invention. For example, endogenous regulatory sequences controlling the expression of proto-oncogenes can be replaced with regulatory sequences such as promoters and/or enhancers which actively express a particular gene in a specific cell type in an organism, i.e., tissue-specific regulatory sequences. In this manner, the expression of a proto-oncogene in a particular cell type, for example in a transgenic animal, can be controlled to determine the effect of oncogene expression in a cell type which does not normally express the proto-oncogene. Alternatively, known viral oncogenes can be inserted into specific sites of the target genome to bring about tissue-specific expression of the viral oncogene. Examples of preferred tissue-specific regulatory sequences are listed in Table IIA. Examples of proto-oncogenes which may be modified by the PNS vectors and methods to produce tissue specific expression and viral oncogenes which may be placed under control of endogenous regulatory sequences are listed in Table IIIA and IIIB, respectively.

TABLE IIIA

Proto-oncogenes involved in human tumors

| Gene | Disease |
| --- | --- |
| c-abl | chronic myelogenous leukemia |
| c-erbB | squamous cell carcinoma |
|  | glial blastoma |
| c-myc | Burkitt's lymphoma |
|  | small cell carcinoma of lung |
|  | carcinoma of breast |
| L-myc | small cell carcinoma of lung |
| N-myc | small cell carcinoma of lung |
|  | neuroblastoma |
| neu | carcinoma of breast |
| C-ras | variety |

TABLE IIIB

Viral oncogenes known to cause tumors when ectopically expressed in mice

| Ha-ras | Sv40Tag |
| HPV-E6 | v-abl |
| HPV-E7 | v-fps |
| PyTag | v-myc |
|  | v-src |

As indicated, the positive-negative selection methods and vectors of the invention are used to modify target DNA sequences in the genome of target cells capable of homologous recombination. Accordingly, the invention may be practiced with any cell type which is capable of homologous recombination. Examples of such target cells include cells derived from vertebrates including mammals such as humans, bovine species, ovine species, murine species, simian species, and other eucaryotic organisms such as filamentous fungi, and higher multicellular organisms such as plants. The invention may also be practiced with lower organisms such as gram positive and gram negative bacteria capable of homologous recombination. However, such lower organisms are not preferred because they generally do not demonstrate significant non-homologous recombination, i.e., random integration. Accordingly, there is little or no need to select against non-homologous transformants.

In those cases where the ultimate goal is the production of a non-human transgenic animal, embryonic stem cells (ES cells) are preferred target cells. Such cells have been manipulated to introduce transgenes. ES cells are obtained from pre-implantation embryos cultured in vitro. Evans, M. J., et al. (1981), *Nature*, 292, 154–156; Bradley, M. O., et al. (1984), *Nature*, 309, 255–258; Gossler, et al. (1986), *Proc. Natl. Acad. Sci. USA*, 83, 9065–9069; and Robertson, et al. (1986), *Nature*, 322, 445–448. PNS vectors can be efficiently introduced into the ES cells by electroporation or microinjection or other transformation methods, preferably electroporation. Such transformed ES cells can thereafter be combined with blastocysts from a non-human animal. The ES cells thereafter colonize the embryo and can contribute to the germ line of he resulting chimeric animal. For review see Jaenisch, R. (1988), *Science*, 240, 1468–1474. In the present invention, PNS vectors are targeted to a specific portion of the ES cell genome and thereafter used to generate chimeric transgenic animals by standard techniques.

When the ultimate goal is gene therapy to correct a genetic defect in an organism such as a human being, the cell type will be determined by the etiology of the particular disease and how it is manifested. For example, hemopoietic stem cells are a preferred cells for correcting genetic defects in cell types which differentiate from such stem cells, e.g. erythrocytes and leukocytes. Thus, genetic defects in globin chain synthesis in erythrocytes such as sickle cell anemia, β-thalassemia and the like may be corrected by using the PNS vectors and methods of the invention with hematopoietic stem cells isolated from an affected patient. For example, if the target DNA in FIG. 3 is the sickle-cell β-globin gene contained in a hematopoietic stem cell and the PNS vector in FIG. 3 is targeted for this gene with the modification shown in the sixth codon, transformed hematopoietic stem cells can be obtained wherein a normal β-globin will be expressed upon differentiation. After correction of the defect, the hematopoietic stem cells may be returned to the bone marrow or systemic circulation of the patient to form a subpopulation of erythrocytes containing normal hemoglobin. Alternatively, hematopoietic stem cells may be destroyed in the patient by way of irradiation and/or chemotherapy prior to reintroduction of the modified hematopoietic stem cell thereby completely rectifying the defect.

Other types of stem cells may be used to correct the specific gene defects associated with cells derived from such stem cells. Such other stem cells include epithelial, liver, lung, muscle, endothelial, menchymal, neural and bone stem cells. Table IV identifies a number of known genetic defects which are amenable to correction by the PNS methods and vectors of the invention.

Alternatively, certain disease states can be treated by modifying the genome of cells in a way which does not correct a genetic defect per se but provides for the supplementation of the gene product of a defective gene. For example, endothelial cells are preferred as targets for human gene therapy to treat disorders affecting factors normally present in the systemic circulation. In model studies using both dogs and pigs endothelial cells have been shown to form primary cultures, to be transformable with DNA in culture, and to be capable of expressing a transgene upon re-implantation in arterial grafts into the host organism. Wilson, et al. (1989), *Science*, 244, 1344; Nabel, et al. (1989), *Science*, 244, 1342. Since endothelial cells form an integral part of the graft, such transformed cells can be used to produce proteins to be secreted into the circulatory system and thus serve as therapeutic agents in the treatment of genetic disorders affecting circulating factors. Examples of such diseases include insulin-deficient diabetes, α-1-antitrypsin deficiency, and hemophilia. Epithelial cells provide a particular advantage in the treatment of factor VIII-deficient hemophilia. These cells naturally produce von Willebrand factor and it has been shown that production of active factor VIII is dependant upon the autonomous synthesis of vWF (Toole, et al. (1986), *Proc. Natl. Acad. Sci. USA*, 83, 5939).

As indicated in Example 4, human endothelial cells from a hemophiliac patient deficient in Factor VIII are modified by a PNS vector to produce an enriched population of transformed endothelial cells wherein the expression of DNA sequences encoding a secretory form of Factor VIII is placed under the control of the regulatory sequences of the endogenous β-actin gene. Such transformed cells are implanted into vascular grafts from the patient. After incorporation of transformed cells, it is grafted back into the vascular system of the patient. The transformed cells secrete Factor XIII into the vascular system to supplement the defect in the patients blood clotting system.

Other diseases of the immune and/or the circulatory system are candidates for human gene therapy. The target tissue, bone marrow, is readily accessible by current technology, and advances are being made in culturing stem cells in vitro. The immune deficiency diseases caused by mutations in the enzymes adenosine deaminase (ADA) and purine nucleotide phosphorylase (PNP), are of particular interest. Not only have the genes been cloned, but cells corrected by PNS gene therapy are likely to have a selective advantage over their mutant counterparts. Thus, ablation of the bone marrow in recipient patients may not be necessary.

The PNS approach is applicable to genetic disorders with the following characteristics: first, the DNA sequence and preferably the cloned normal gene must be available; second, the appropriate, tissue relevant, stem cell or other appropriate cell must be available. Below is Table IV listing some of the known genetic diseases, the name of the cloned gene, and the tissue type in which therapy may be appropriate. These and other genetic disease amenable to the PNS methods and vectors of the invention have been reviewed. See Friedman (1989), *Science*, 244, 1275; Nichols, E. K. (1988), *Human Gene Therapy* (Harvard University Press); and *Cold Springs Harbor Symposium on Quantitative Biology*, Vol. 11 (1986), "The Biology of Homo Sapiens" (Cold Springs Harbor Press).

TABLE IV

Human Genetic Diseases in Which the Disease Locus has been Cloned

| Disease | Gene | Target Tissue |
|---|---|---|
| α1-anti-trypsin disease | α1-anti trypsin | liver |
| Gaucher Disease | glucocerebrosidase | bone marrow |
| Granulocyte Actin Deficiency | Granulocyte Actin | bone marrow |
| Immunodeficiency | Adenosine deaminase | bone marrow |
| Immunodeficiency | Purine nucleoside | bone marrow |
| Muscular Dystrophy | most likely dystropin gene | skeletal muscle |
| Phenylketonuria | Phenylalanine hydroxylase | liver |
| Sickle Cell Anemia | β-globin | bone marrow |
| Thalassemia | globin | bone marrow |
| Hemophilia | various clotting factors | bone marrow/endothelial cells |
| Familial hypercholesterolemia | low density lipoprotein receptor | liver/endo-endothelial cells |

As indicated, genetic defects may be corrected in specific cell lines by positioning the positive selection marker (the second DNA sequence in the PNS vector) in an untranslated region such as an intron near the site of the genetic defect together with flanking segments to correct the defect. In this approach, the positive selection marker is under its own regulatory control and is capable of expressing itself without substantially interfering with the expression of the targeted gene. In the case of human gene therapy, it may be desirable to introduce only those DNA sequences which are necessary to correct the particular genetic defect. In this regard, it is desirable, although not necessary, to remove the residual positive selection marker which remains after correction of the genetic defect by homologous recombination.

The removal of a positive selection marker from a genome in which homologous insertion of a PNS vector has occurred can be accomplished in many ways. For example, the PNS vector can include a second negative selection marker contained within the second DNA sequence. This second negative selection marker is different from the first negative selection marker contained in the fourth DNA sequence. After homologous integration, a second modified target DNA sequence is formed containing the third DNA encoding both the positive selection marker and the second negative selection marker. After isolation and purification of the first transformed target cells by way of negative selection against transformed cells containing the first negative selection marker and for those cells containing the positive selection marker, the first transformed target cells are subjected to a second cycle of homologous recombination. In this second cycle, a second homologous vector is used which contains all or part of the first and second DNA sequence of the PNS vector (encoding the second modification in the target DNA) but not those sequences encoding the positive and second negative selection markers. The second negative selection marker in the first transformed target cells is then used to select against unsuccessful transformants and cells wherein the second homologous vector is randomly integrated into the genome. Homologous recombination of this second homologous vector, however, with the second modified target DNA sequence results in a second transformed target cell type which does not contain either the positive selection marker or the second negative selection marker but which retains the modification encoded by the first and/or second DNA sequences. Cells which have not homologously integrated the second homologous vector are selected against using the second negative selection marker.

The PNS vectors and methods of the invention are also applicable to the manipulation of plant cells and ultimately the genome of the entire plant. A wide variety of transgenic plants have been reported, including herbaceous dicots, woody dicots and monocots. For a summary, see Gasser, et al. (1989), *Science*, 244, 1293–1299. A number of different gene transfer techniques have been developed for producing such transgenic plants and transformed plant cells. One technique used *Agrobacterium tumefaciens* as a gene transfer system. Rogers, et al. (1986), *Methods Enzymol.*, 118, 627–640. A closely related transformation utilizes the bacterium *Agrobacterium rhizogenes*. In each of these systems a Ti or Ri plant transformation vector can be constructed containing border regions which define the DNA sequence to be inserted into the plant genome. These systems previously have been used to randomly integrate exogenous DNA to plant genomes. In the present invention, an appropriate PNS vector may be inserted into the plant transformation vector between the border sequences defining the DNA sequences transferred into the plant cell by the Agrobacterium transformation vector.

Preferably, the PNS vector of the invention is directly transferred to plant protoplasts by way of methods analogous to that previously used to introduce transgenes into protoplasts. See, e.g. Paszkowski, et al. (1984), *EMBO J.*, 3, 2717–2722; Hain, et al. (1985), *Mol. Gen. Genet.*, 199, 161–168; Shillito, et al. (1985), *Bio./Technology*, 3, 1099–1103; and Negrutiu, et al. (1987), *Plant Mol. Bio., 8,* 363–373. Alternatively, the PNS vector is contained within a liposome which may be fused to a plant protoplast (see, e.g. Deshayes, et al. (1985), *EMBO J.,* 4, 2731–2738) or is directly inserted to plant protoplast by way of intranuclear microinjection (see, e.g. Crossway. et al. (1986), *Mol. Gen Genet.,* 202, 179–185, and Reich, et al. (1986), *Bio/Technology,* 4, 1001–1004). Microinjection is the preferred method for transfecting protoplasts. PNS vectors may also be microinjected into meristematic inflorenscences. De la Pena et al. (1987), *Nature,* 325, 274–276. Finally, tissue explants can be transfected by way of a high velocity microprojectile coated with the PNS vector analogous to the methods used for insertion of transgenes. See, e.g. Vasil (1988), *Bio/Technology,* 6, 397; Klein, et al. (9187), *Nature,* 327, 70; Klein, et al. (1988), *Proc. Natl. Acad. Sci. USA,* 85, 8502; McCabe, et al. (1988), *Bio/Technology,* 6, 923; and Klein, et al., *Genetic Engineering,* Vol 11, J. K. Setlow editor (Academic Press, N.Y., 1989). Such transformed explants can be used to regenerate for example various serial crops. Vasil (1988), *Bio/Technology,* 6, 397.

Once the PNS vector has been inserted into the plant cell by any of the foregoing methods, homologous recombination targets the PNS vector to the appropriate site in the plant genome. Depending upon the methodology used to transfect, positive-negative selection is performed on tissue cultures of the transformed protoplast or plant cell. In some instances, cells amenable to tissue culture may be excised from a transformed plant either from the F0 or a subsequent generation.

The PNS vectors and method of the invention are used to precisely modify the plant genome in a predetermined way. Thus, for example, herbicide, insect and disease resistance may be predictably engineered into a specific plant species to provide, for example, tissue specific resistance, e.g., insect resistance in leaf and bark. Alternatively, the expression levels of various components within a plant may be modified by substituting appropriate regulatory elements to change the fatty acid and/or oil content in seed, the starch content within the plant and the elimination of components contributing to undesirable flavors in food. Alternatively, heterologous genes may be introduced into plants under the predetermined regulatory control in the plant to produce various hydrocarbons including waxes and hydrocarbons used in the production of rubber.

The amino acid composition of various storage proteins in wheat and corn, for example, which are known to be deficient in lysine and tryptophan may also be modified. PNS vectors can be readily designed to alter specific codons within such storage proteins to encode lysine and/or tryptophan thereby increasing the nutritional value of such crops. For example, the zein protein in corn (Pederson et al. (1982), *Cell,* 2, 1015) may be modified to have a higher content of lysine and tryptophan by the vectors and methods of the invention.

It is also possible to modify the levels of expression of various positive and negative regulatory elements controlling the expression of particular proteins in various cells and organisms. Thus, the expression level of negative regulatory elements may be decreased by use of an appropriate promotor to enhance the expression of a particular protein or proteins under control of such a negative regulatory element. Alternatively, the expression level of a positive regulatory protein may be increased to enhance expression of the regulated protein or decreased to reduce the amount of regulated protein in the cell or organism.

The basic elements of the PNS vectors of the invention have already been described. The selection of each of the DNA sequences comprising the PNS vector, however, will depend upon the cell type used, the target DNA sequence to be modified and the type of modification which is desired.

Preferably, the PNS vector is a linear double stranded DNA sequence. However, circular closed PNS vectors may also be used. Linear vectors are preferred since they enhance the frequency of homologous integration into the target DNA sequence. Thomas, et al. (1986), *Cell,* 44, 49.

In general, the PNS vector (including first, second, third and fourth DNA sequences) has a total length of between 2.5 kb (2500 base pairs) and 1000 kb. The lower size limit is set by two criteria. The first of these is the minimum necessary length of homology between the first and second sequences of the PNS vector and the target locus. This minimum is approximately 500 bp (DNA sequence 1 plus DNA sequence 2). The second criterion is the need for functional genes in the third and fourth DNA sequences of the PNS vector. For practical reasons, this lower limit is approximately 1000 bp for each sequence. This is because the smallest DNA sequences encoding known positive and negative selection markers are about 1.0–1.5kb in length.

The upper limit to the length of the PNS vector is determined by the state of the technology used to manipulate DNA fragments. If these fragments are propagated as bacterial plasmids, a practical upper length limit is about 25 kb; if propagated as cosmids, the limit is about 50 kb, if propagated as YACs (yeast artificial chromosomes) the limit approaches 1000 kb (Burke, et al. (1987), *Science,* 236, 806).

Within the first and second DNA sequences of the PNS vector are portions of DNA sequence which are substantially homologous with sequence portions contained within the first and second regions of the target DNA sequence. The degree of homology between the vector and target sequences influences the frequency of homologous recombination between the two sequences. One hundred percent sequence homology is most preferred, however, lower sequence homology can be used to practice the invention. Thus, sequence homology as low as about 80% can be used. A practical lower limit to sequence homology can be defined functionally as that amount of homology which if further reduced does not mediate homologous integration of the PNS vector into the genome. Although as few as 25 bp of 100% homology are required for homologous recombination in mammalian cells (Ayares, et al. (1986), *Genetics,* 83, 5199–5203), longer regions are preferred, e.g., 500 bp, more preferably, 5000 bp, and most preferably, 25000 bp for each homologous portion. These numbers define the limits of the individual lengths of the first and second sequences. Preferably, the homologous portions of the PNS vector will be 100% homologous to the target DNA sequence, as increasing the amount of non-homology will result in a corresponding decrease in the frequency of gene targeting. If non-homology does exist between the homologous portion of the PNS vector and the appropriate region of the target DNA, it is preferred that the non-homology not be spread throughout the homologous portion but rather in discrete areas of the homologous portion. It is also preferred that the homologous portion of the PNS vector adjacent to the negative selection marker (fourth or fifth DNA sequence) be 100% homologous to the corresponding region in the target DNA. This is to ensure maximum discontinuity between homologous and non-homologous sequences in the PNS vector.

Figure 4:
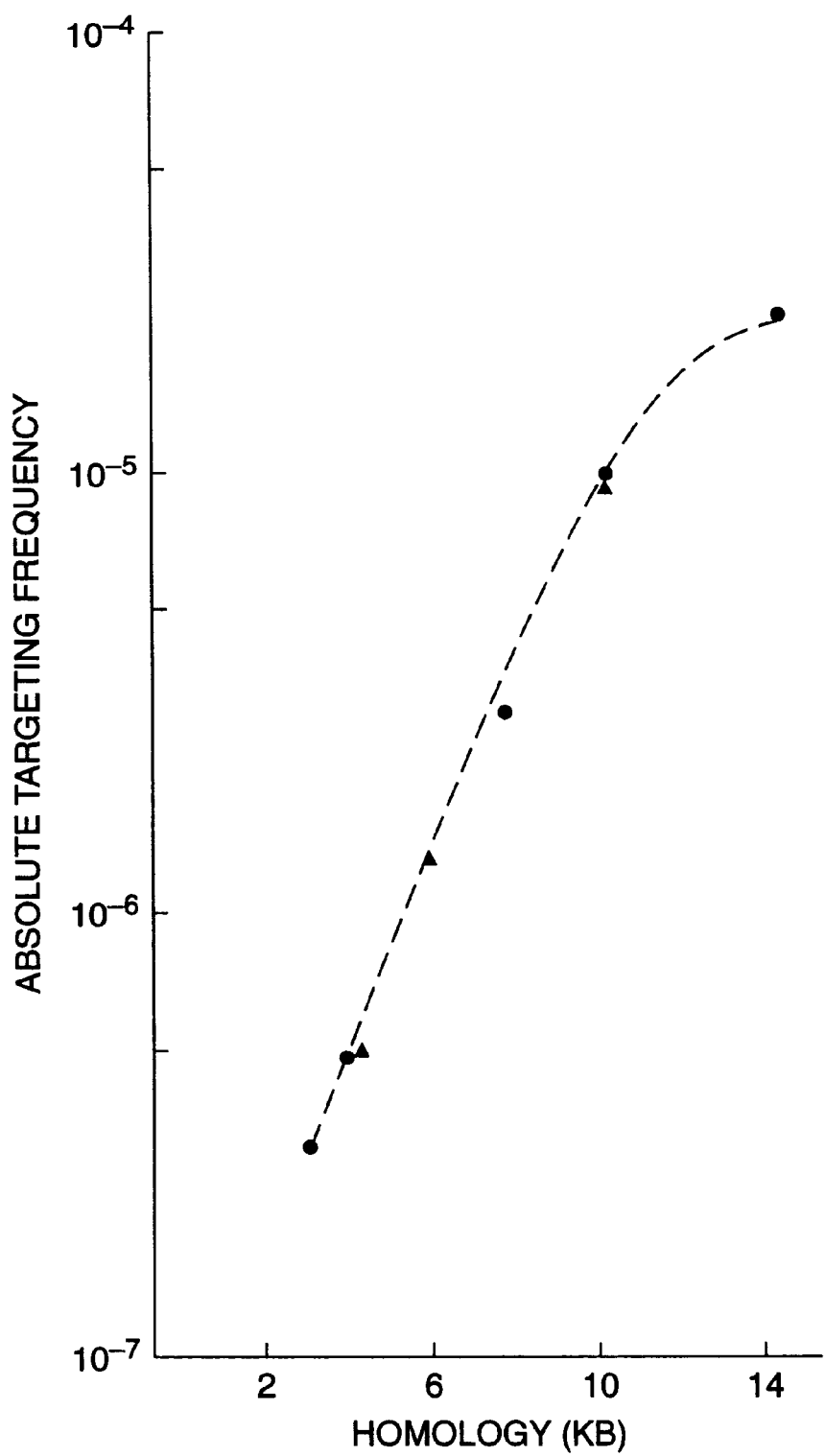
FIG. 4 is a graphic representation of the absolute frequency of homologous recombination versus the amount of 100% sequence homology in the first and second DNA sequences of the PNS vectors of the invention.

Increased frequencies of homologous recombination have been observed when the absolute amount of DNA sequence in the combined homologous portions of the first and second DNA sequence are increased. FIG. 4 depicts the targeting frequency of the Hprt locus as a function of the extent of homology between an appropriate PNS vector and the endogenous target. A series of replacement (▲) and insertion (●) Hprt vectors were constructed that varied in the extent of homology to the endogenous Hprt gene. Hprt sequences in each vector were interrupted in the eighth exon with the neomycin resistance gene. The amount of Hprt sequence 3' to the neo gene was kept constant to the amount of Hprt sequence 5' to the neo was varied. The absolute frequency of independent targeting events per total ES cells electroporated is plotted in FIG. 4 on the logarithmic scale as a function of the number of kilobases of Hprt sequence contained within the PNS vectors. See Capecchi, M. R. (1989), *Science*, 244, 1288–1292.

As previously indicated, the fourth DNA sequence containing the negative selection marker should have sufficient non-homology to the target DNA sequence to prevent homologous recombination between the fourth DNA sequence and the target DNA. This is generally not a problem since it is unlikely that the negative selection marker chosen will have any substantial homology to the target DNA sequence. In any event, the sequence homology between the fourth DNA sequence and the target DNA sequence should be less than about 50%, most preferably less than about 30%.

A preliminary assay for sufficient sequence non-homology between the fourth DNA sequence and the target DNA sequence utilizes standard hybridization techniques. For example, the particular negative selection marker may be appropriately labeled with a radioisotope or other detectable marker and used as a probe in a Southern blot analysis of the genomic DNA of the target cell. If little or no signal is detected under intermediate stringency conditions such as 3×SSC when hybridized at about 55° C., that negative selection marker should be functional in a PNS vector designed for homologous recombination in that cell type. However, even if a signal is detected, it is not necessarily indicative that particular negative selection cannot be used in a PNS vector targeted for that genome. This is because the negative selection marker may be hybridizing with a region of the genome which is not in proximity with the target DNA sequence. Since the target DNA sequence is defined as those DNA sequences corresponding to first, second, third, and in some cases, fourth regions of the genome, Southern blots localizing the regions of the target DNA sequence may be performed. If the probe corresponding to the particular negative selection marker does not hybridize to these bands, it should be functional for PNS vectors directed to these regions of the genome.

Hybridization between sequences encoding the negative selection marker and the genome or target regions of a genome, however, does not necessarily mean that such a negative selection marker will not function in a PNS vector. The hybridization assay is designed to detect those sequences which should function in the PNS vector because of their failure to hybridize to the target. Ultimately, a DNA sequence encoding a negative selection marker is functional in a PNS vector if it is not integrated during homologous recombination regardless of whether or not it hybridizes with the target DNA.

It is also possible that high stringency hybridization can be used to ascertain whether genes from one species can be targeted into related genes in a different species. For example, preliminary gene therapy experiments may require that human genomic sequences replace the corresponding related genomic sequence in mouse cells. High stringency hybridization conditions such as 0.1×SSC at about 68° C. can be used to correlate hybridization signal under such conditions with the ability of such sequences to act as homologous portions in the first and second DNA sequence of the PNS vector. Such experiments can be routinely performed with various genomic sequences having known differences in homology. The measure of hybridization may therefore correlate with the ability of such sequences to bring about acceptable frequencies of recombination.

Table I identifies various positive and negative selection markers which may be used respectively in the third and fourth DNA sequences of the PNS vector together with the conditions used to select for or against cells expressing each of the selection markers. As for animal cells such as mouse L cells, ES cells, preferred positive selection markers include DNA sequences encoding neomycin resistance and hygromycin resistance, most preferably neomycin resistance. For plant cells preferred positive selection markers include neomycin resistance and bleomycin resistance, most preferably neomycin resistance.

For animal cells, preferred negative selection markers include gpt and HSV-tk, most preferably HSV-tk. For plant cells, preferred negative selection markers include Gpt and HSV-tk. As genes responsible for bacterial and fungal pathogenesis in plants are cloned, other negative markers will become readily available.

As used herein, a "positive screening marker" refers to a DNA sequence used in a phage rescue screening method to detect homologous recombination. An example of such a positive screening marker is the supF gene which encodes a tyrosine transfer RNA which is capable of suppressing amber mutations. See Smithies, et al. (1985), *Nature*, 317, 230–234.

The following is presented by way of example and is not to be construed as a limitation on the scope of the invention.

EXAMPLE 1

Inactivation at the Int-2 Locus in Mouse ES Cells

1. PNS Vector Construction

Figure 5A:
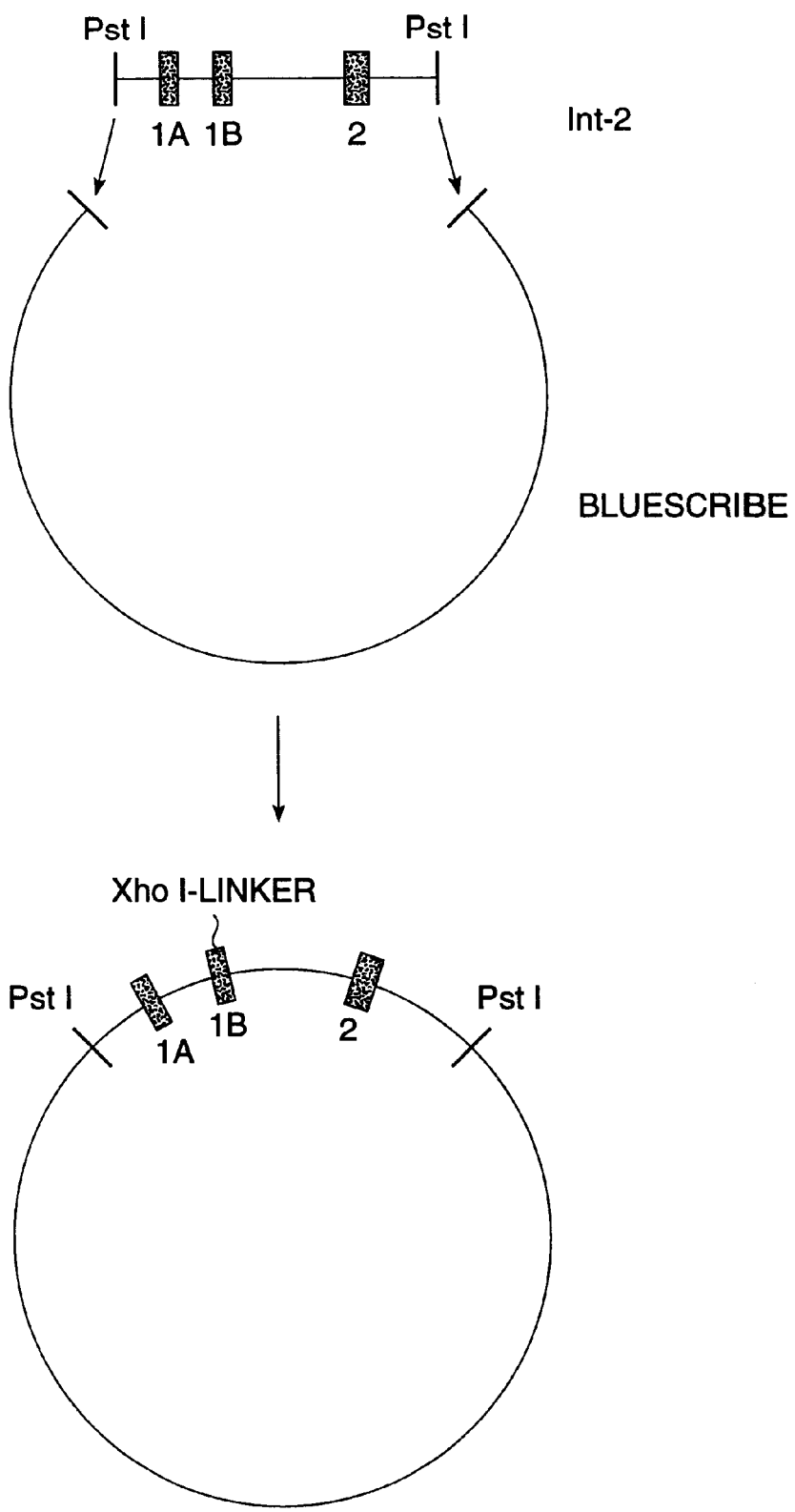
FIGS. 5a, 5b, 5c and 5d depict the construction of a PNS vector used to disrupt the INT-2 gene.
Figure 5B:
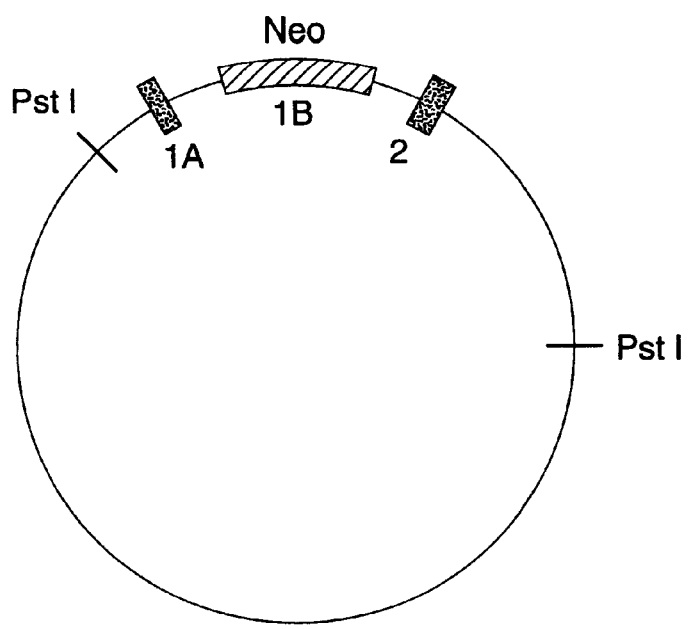
Figure 5B:
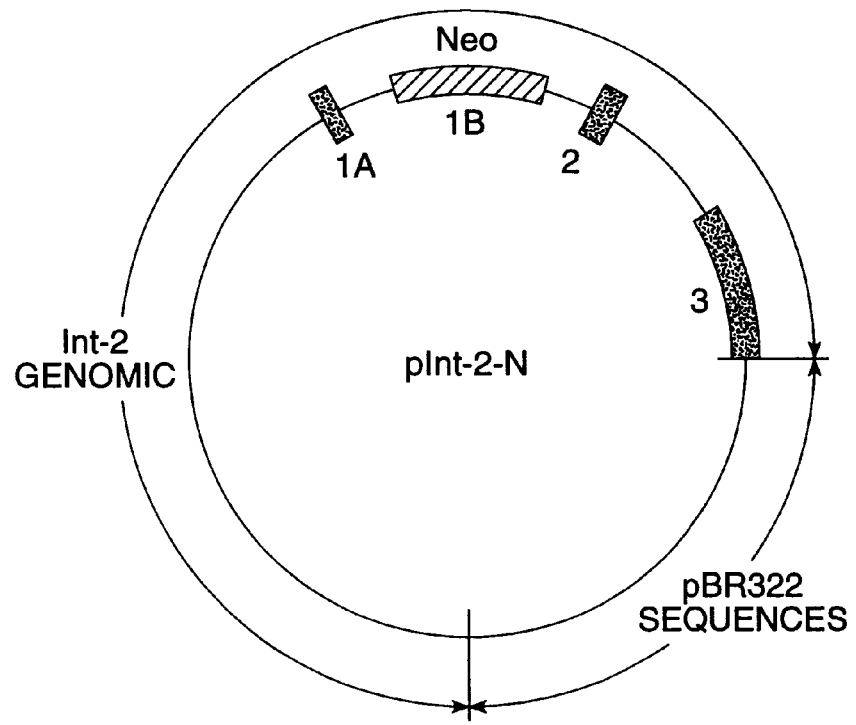
Figure 5C:
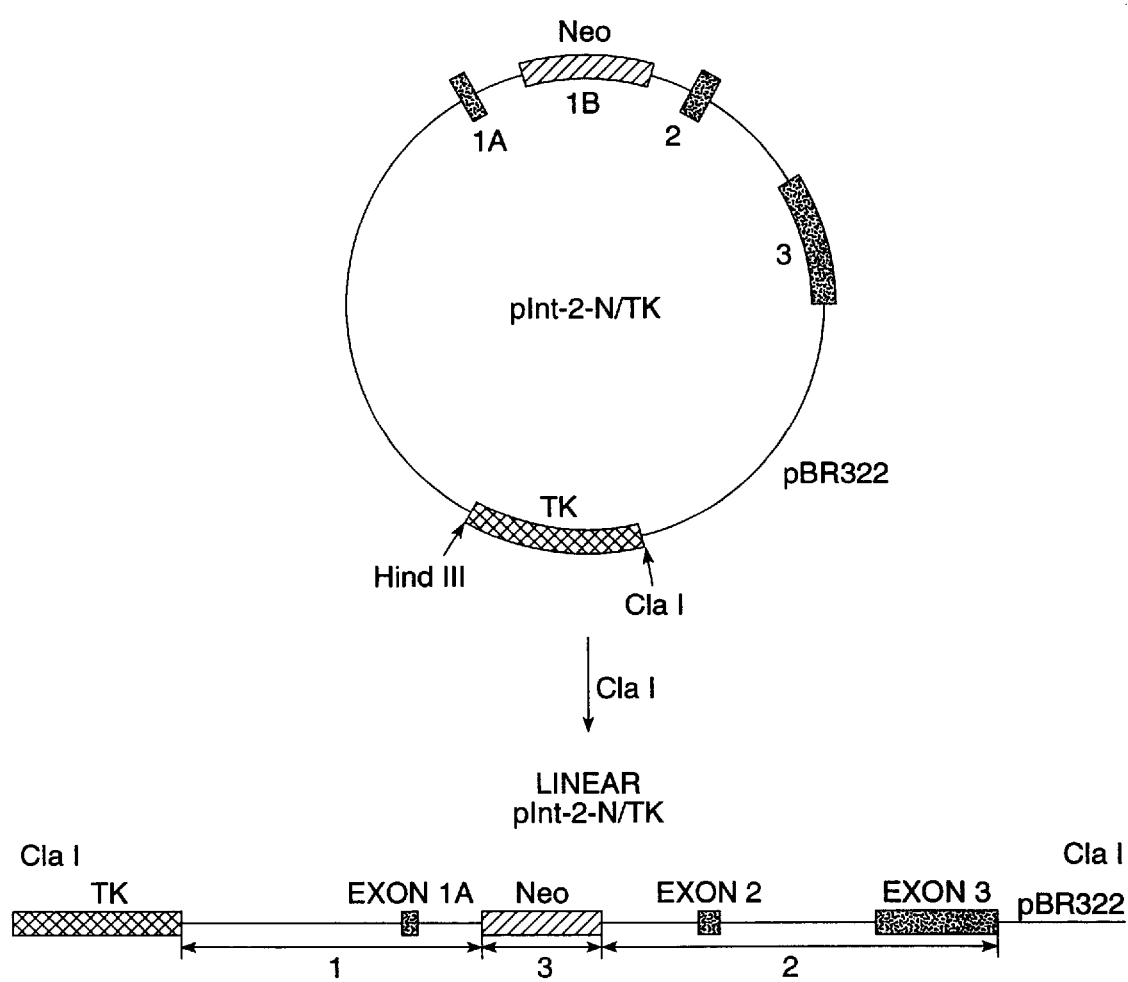
Figure 5D:

The PNS vector, pINT-2-N/TK, is described in Mansour, et al. (1988), *Nature*, 336, 349. This vector was used to disrupt the proto-oncogene, INT-2, in mouse ES cells. As shown in FIG. 5c, it contains DNA sequences 1 and 2 homologous to the target INT-2 genomic sequences in mouse ES cells. These homologous sequences were obtained from a plasmid referred to as pAT-153 (Peters, et al. (1983), *Cell*, 33, 369). DNA sequence 3, the positive selection moiety of the PNS vector was the Neo gene from the plasmid pMCINeo described in Thomas, et al. (1987), *Cell*, 51, 503; DNA sequence 4, the negative selection element of the vector, was the HSV-TK gene derived from the plasmid pIC-19-R/TK which is widely available in the scientific community. Plasmid pIC19R/MC1-TK (FIG. 5d) contains the HSV-TX gene engineered for expression in ES cells (Mansour, et al. (1988), *Nature*, 336, 348–352). The TK gene, flanked by a duplication of a mutant polyoma virus enhancer, PYF441, has been inserted into the vector, pIC19R (Marsh, et al. (1984), *Gene*, 32, 481–485) between the XhoI and the HindIII sites. The map of plasmid pIC19R/MC1-TK is shown in FIG. 5d. The enhancer sequence is as follows:

5'
CTCGAGCAGT GTGGTTTTCA AGAGGAAGCA AAAGCCTCT CCACCCAGGC
CTGGAATGIT TCCACCCAAT GTCGAGCAGT GTGGTTTTGC AAGAGGAAGC

AAAAAGCCTC TCCACCCAGG CCTGGAATGT TTC-CACCCAA TCTCGAG 3'

The 5' end is an XhoI restriction enzyme site, the 3' end is contiguous with the HSV-TK gene. The HSV-TK sequences are from nucleotides 92–1799 (McKnight (1980), *Nucl. Acids. Res.*, 8, 5949–5964) followed at the 3' end by a HindIII linker. The plasmid pIC19R is essentially identical to the pUC vectors, with an alternative poly-linker as shown in FIG. 5d.

Construction of the vector, pINT-2-N/TK involved five sequential steps as depicted in FIG. 5. First, a 3,965 bp PstI fragment containing exon 1b, was excised from pAT153 and inserted into the PstI site of Bluescribe° (Stratagene of LaJolla, Calif.), an Amp$^R$ bacterial plasmid containing a multi-enzyme, cloning polylinker. Second, a synthetic XhoI linker of sequence

was inserted into the ApaI site on exon 1b. Third, the XhoI-SalI Neo$^r$-fragment from pMCI Neo was inserted into the XhoI linker in exon 1b. Fourth, the 3,965 bp INT-2 Pst fragment containing the Neo$^r$ gene was reinserted into pAT153, to generate the plasmid pINT-2-N as shown in FIG. 5b. This plasmid also includes the third exon of the int-2 gene. Fifth, the ClaI-HindII HSV-tk fragment from pIC-19-R/TK was inserted into ClaI-HindII digested pINT2-N, creating the final product, pINT-2-N/TK. This vector was linearized by digestion with ClaI prior to its introduction into ES cells.

2. Generation of ES Cells

ES cells were derived from two sources. The first source was isolation directly from C57B1/6 blastocysts (Evans, et al. (1981), *Nature*, 9, 154–156) except that primary embryonic fibroblasts (Doetschman, et al. (1985), *J. Embryol. Exp. Morphol.*, 87, 27–45) were used as feeders rather than STO cells. Briefly, 2.5 days postpregnancy mice were ovariectomized, and delayed blastocysts were recovered 4–6 days later. The blastocysts were cultured on mitomycin C-inactivated primary embryonic fibroblasts. After blastocyst attachment and the outgrowth of the trophectoderm, the ICM-derived clump was picked and dispersed by trypsin into clumps of 3–4 cells and put onto new feeders. All culturing was carried out in DMEM plus 20% FCS and $10^{-4}$ β-mercaptoethanol. The cultures were examined daily. After 6–7 days in culture, colonies that still resembled ES cells were picked, dispersed into single cells, and replated on feeders. Those cell lines that retained the morphology and growth characteristic of ES cells were tested for pluripotency in vitro. These cell lines were maintained on feeders and transferred every 2–3 days.

The second method was to utilize one of a number of ES cell lines isolated from other laboratories, e.g., CC1.2 described by Kuehn, et al. (1987), *Nature*, 326, 295. The cells were grown on mitomycin C-inactivated STO cells. Cells from both sources behaved identically in gene targeting experiments.

3. Introduction of PNS Vector pINT-2-N/TK into ES cells

The PNS vector pINT-2-N/TK was introduced into ES cells by electroporation using the Promega Biotech X-Cell 2000. Rapidly growing cells were trypsinized, washed in DMEM, counted and resuspended in buffer containing 20 mM HEPES (pH 7.0), 137 mM NaCl, 5 mM KCl, 0.7 mM $Na_2HPO_4$, 6 mM dextrose, and 0.1 MM β-mercaptoethanol. Just prior to electroporation, the linearized recombinant vector was added. Approximately 25 μg of linearized PNS vector was mixed with 107 ES cells in each 1 ml-cuvette.

Cells and DNA were exposed to two sequential 625 V/cm pulses at room temperature, allowed to remain in the buffer for 10 minutes, then plated in non-selective media onto feeder cells.

4. Selection of ES Cells Containing a Targeted Disruption of the Int-2 Locus

Following two days of non-selective growth, the cells were trypsinized and replated onto G418 (250 μg/ml) media. The positive-selection was applied alone for three days, at which time the cells were again trypsinized and replated in the presence of G418 and either gancyclovir ($2\times10^{-6}$ M) (Syntex, Palo Alto, Calif.) or 1-(2-deoxy-2-fluoro-β-D-arabino-furanosyl-5-iodouracil (F.I.A.U.) ($1\times10^{-6}$ M) (Bristol Myers). When the cells had grown to confluency, each plate of cells was divided into two aliquots, one of which was frozen in liquid $N_2$, the other harvested for DNA analysis.

5. Formation of INT-2 Disrupted Transgenic Mice

Those transformed cells determined to be appropriately modified by the PNS vector were grown in non-selective media for 2–5 days prior to injection into blastocysts according to the method of Bradley in *Teratocarcinomas and embryonic stem cells, a practical approach*, edited by E. J. Robertson, IRL Press, Oxford (1987), p. 125.

Blastocysts containing the targeted ES cells were implanted into pseudo-pregnant females and allowed to develop to term. Chimaeric offspring were identified by coat-color markers and those males showing chimaerism were selected for breeding offspring. Those offspring which carry the mutant allele can be identified by coat color, and the presence of the mutant allele reaffirmed by DNA analysis by tail-blot, DNA analysis.

EXAMPLE 2

Disruption at the Hox1.4 Locus in Mouse ES Cells

Disruption of the hox1.4 locus was performed by methods similar to those described to disrupt the int-2 locus. There were two major differences between these two disruption strategies. First, the PNS vector, pHOX1.4N/TK-TK2 (FIG. 6), used to disrupt the hox1.4 locus contained two negative selection markers, i.e., a DNA sequence 5 encoding a second negative selection marker was included on the PNS vector at the end opposite to DNA sequence 4 encoding the first negative selection marker. DNA sequence 5 contained the tk gene isolated from HSV-type 2. It functioned as a negative-selectable marker by the same method as the original HSV-tk gene, but the two tk genes are 20% non-homologous. This non-homology further inhibits recombination between DNA sequences 4 and 5 in the vector which might have inhibited gene-targeting. The second difference between the int-2 and the hox1.4 disruption strategies is that the vector pHOX1.4N/TK-TK2 contains a deletion of 1000 bp of hox1.4 sequences internal to the gene, i.e., DNA sequences 1 and 2 are not contiguous.

The HSV-tk2 sequences used in this construction were obtained from pDG504 (Swain, M. A. et al. (1983), *J. Virol.*, 46, 1045). The structural TK gene from pDG504 was inserted adjacent to the same promoter/enhancer sequences used to express both the Neo and HSV-tk genes, to generate the plasmid pIC20H/TK2.

Figure 6:
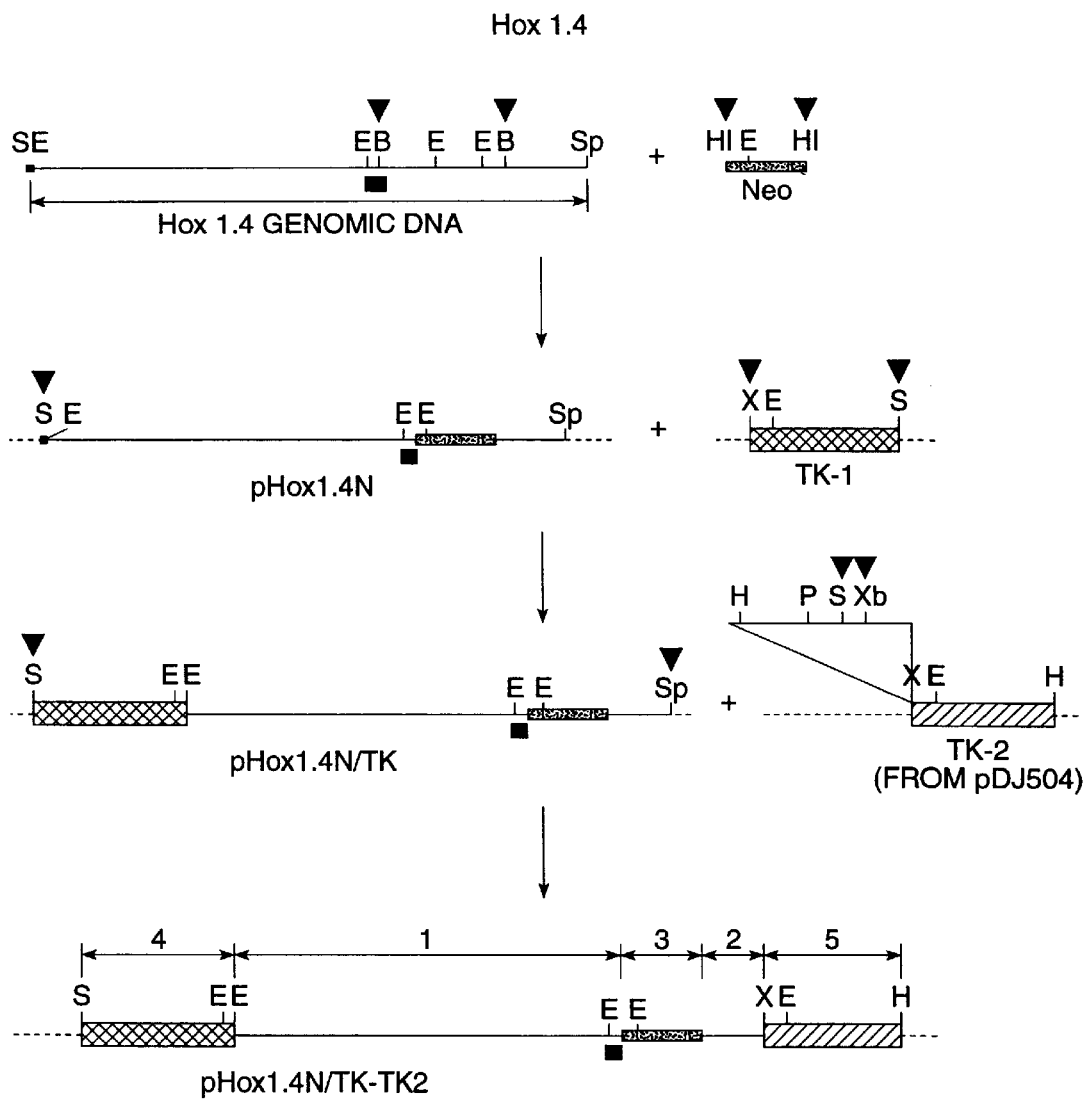
FIG. 6 depicts the construction of a PNS vector used to disrupt the HOX1.4 gene.

Construction of pHOX1.4N/TK-TK2 proceeded in five sequential steps as depicted in FIG. 6. First a clone containing hox1.4 sequences was isolated from a genomic A library. The A library was constructed by inserting EcoRI partially digested mouse DNA into the A-DASH® (Stratagene) cloning phage. The hox1.4 containing phage were identified by virtue of their homology to a synthetic oligonucleotide synthesized from the published sequence of the hox1.4 locus. Tournier-Lasserve, et al. (1989), *Mol. Cell Biol.,* 9, 2273. Second, a 9 kb SalI-SpeI fragment containing the hox1.4 homeodomain was inserted into Bluescribe®. Third, a 1 kb BglII fragment within the hox1.4 locus was replaced with the Neo$^r$ gene isolated from pMCl Neo, creating the plasmid pHOX1.4N. Fourth, the XhoI-SalI fragment by HSV-tk from pIC19R/TK was inserted into the SalI site of pHOX1.4N, generating the plasmid pHOX1.4N/TK. Fifth, the SalI-SpeI fragment from pHOX1.4N/TK was inserted into a SalI-XbaI digest of the plasmid pIC20HTK2, generating the final product, pHOX1.4N/TK/TK2. This vector was digested with SalI to form a linear PNS vector which was transfected into mouse ES cells as described in Example 1. Positive-negative selection and the method of forming transgenic mice was also as described in Example 1. Southern blots of somatic cells demonstrate that the disrupted hox1.4 gene was transferred to transgenic offspring.

EXAMPLE 3

Inactivation of Other Hox Genes

The methods described in Examples 1 and 2 have also been used to disrupt the hox1.3, hox1.6, hox2.3, and int-1 loci in ES cells. The genomic sequences for each of these loci (isolated from the same -Dash library containing the hox1.4 clone) were used to construct PNS vectors to target disruption of these genes. All of these PNS vectors contain the Neo gene from pMCi-Neo as the positive selection marker and the HSV-tk and HSV-tk2 sequences as negative selection markers.

TABLE V

Other Murine Developmental Genes Inactivated by PNS

| Locus | Genomic Fragment | Sequence Ref. | Neo-Insertion Site |
|---|---|---|---|
| hox1.3 | 11kb Xba-HindIII | Tournier-lasserve, et al. (1989), MCE, 9, 2273 | EcoRI-site in homeo-domain |
| hox1.6 | 13kb partial RI | Baron, et al. (1987), EMBO, 6, 2977 | BglII-site in homeo-domain |
| hox2.3 | 12kb BamHI | Hart, et al. (1987), Genomics, 1, 182 | BglII-site in homeo-domain |
| int-1 | 13kb BglII | Van Ooyen et al. (1984), Cell, 39, 233 | XhoI-site in exon 2 |

EXAMPLE 4

Vascular Graft Supplementing Factor VIII

Figure 7A:
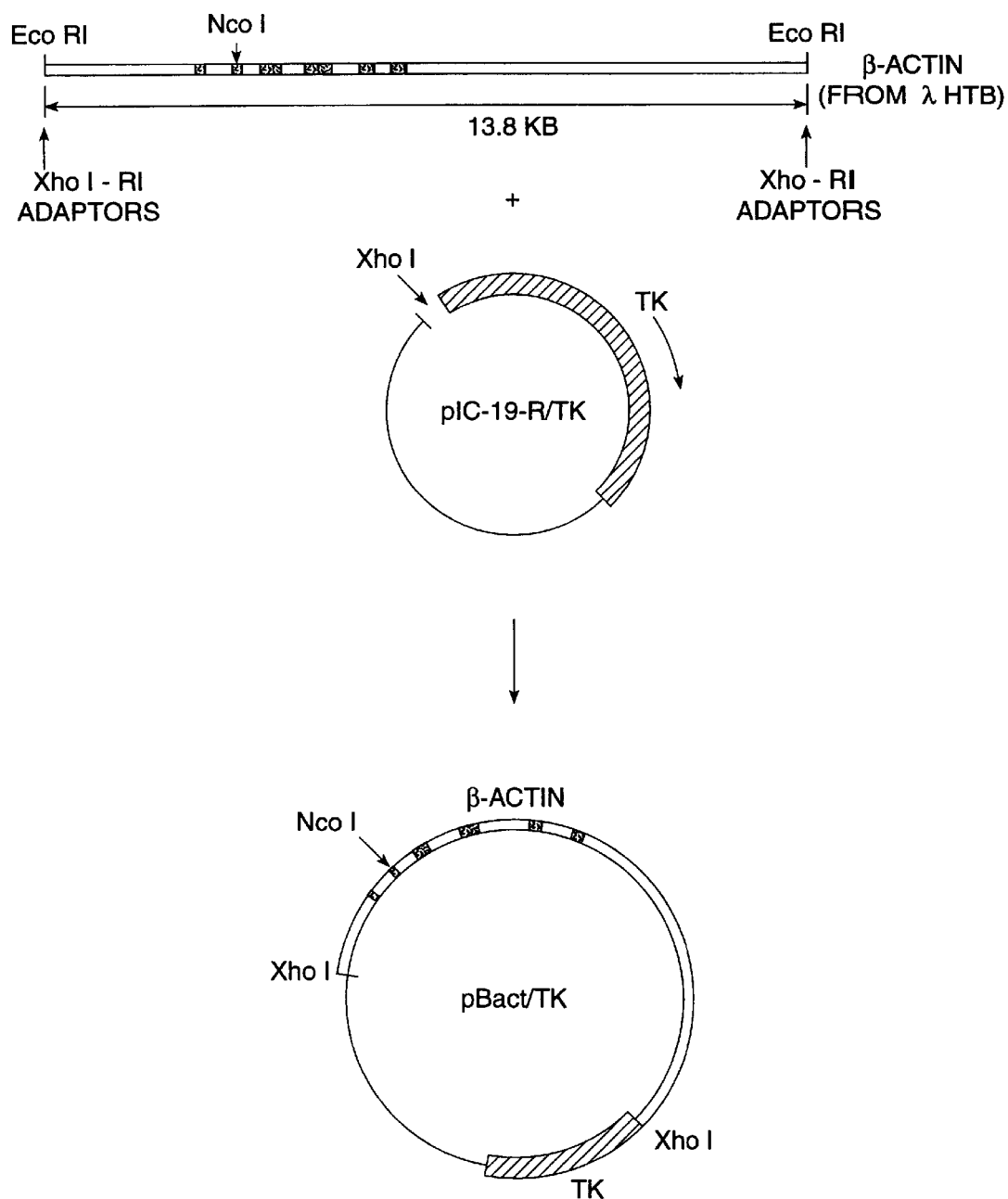
FIGS. 7A, 7B and 7C depict the construction of a PNS vector used to transform endothelial cells to express factor VIII.

In this example, a functional factor VIII gene is targeted by a PNS vector to the β-actin locus in human endothelial cells. When so incorporated, the expression of factor VIII is controlled by the β-actin promoter, a promoter known to function in nearly all somatic cells, including fibroblasts, epithelial and endothelial cells. PNS vector construction is as follows: In step IA (FIG. 7A), the 13.8 kb EcoRI fragment containing the entire human β-actin gene from the λ-phage, 14TB (Leavitte, et al. (1984), *Mol. Cell Bio.,* 4, 1961) is inserted, using synthetic Ecorl/XhoI adaptors, into the XhoI site of the TK vector, pIC-19-R/TK to form plasmid pBact/TK. See FIG. 7A.

Figure 7B:
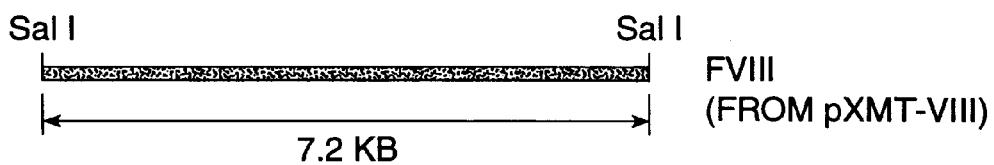
Figure 7B:
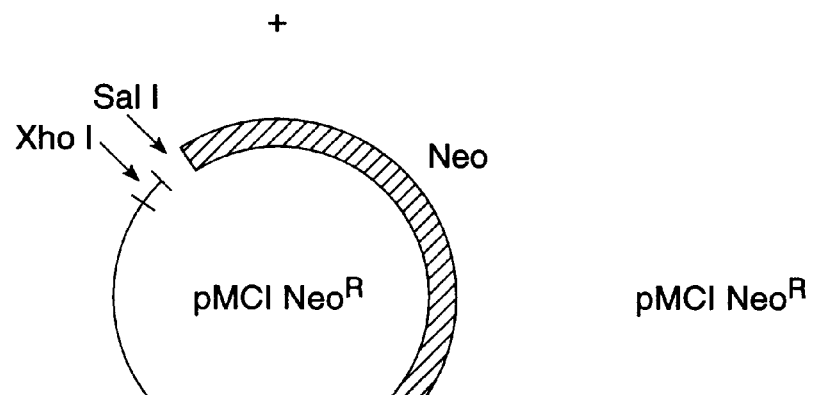
Figure 7B:
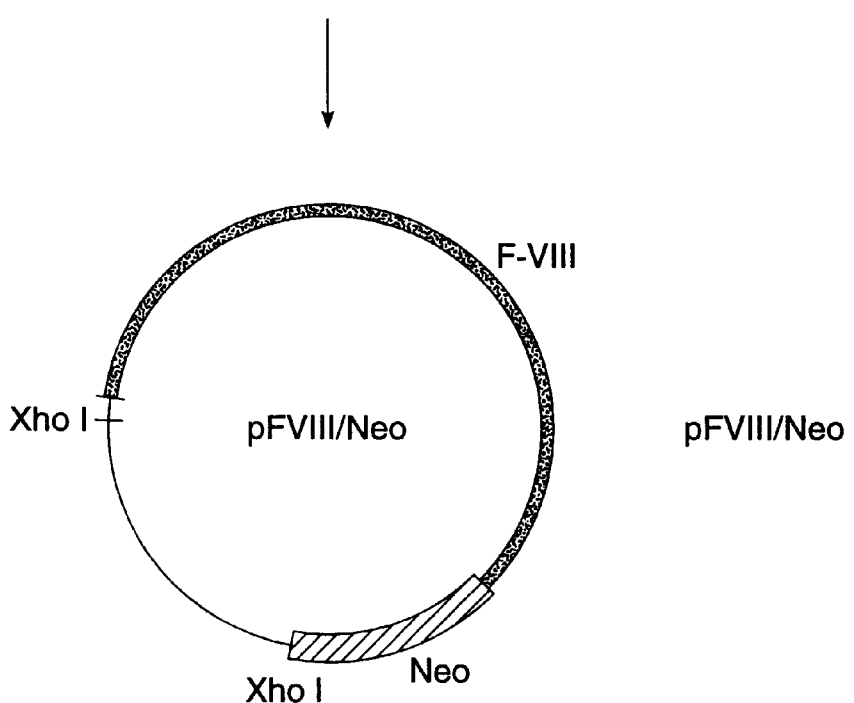

In step 1 B (FIG. 7B), the 7.2 kb SalI fragment from a factor VIII cDNA clone including its native signal sequence (Kaufman, et al. (1988), *JBC,* 263, 6352; Toole, et al. (1986), *Proc. Natl. Acad. Sci. USA,* 83, 5939) is inserted next to the Neo$^r$ gene in a pMCI derivative plasmid. This places the neo$^r$ gene (containing its own promoter/enhancer) 3' to the polyadenylation site of factor VIII. This plasmid is designated pFVIII/Neo.

Figure 7C:
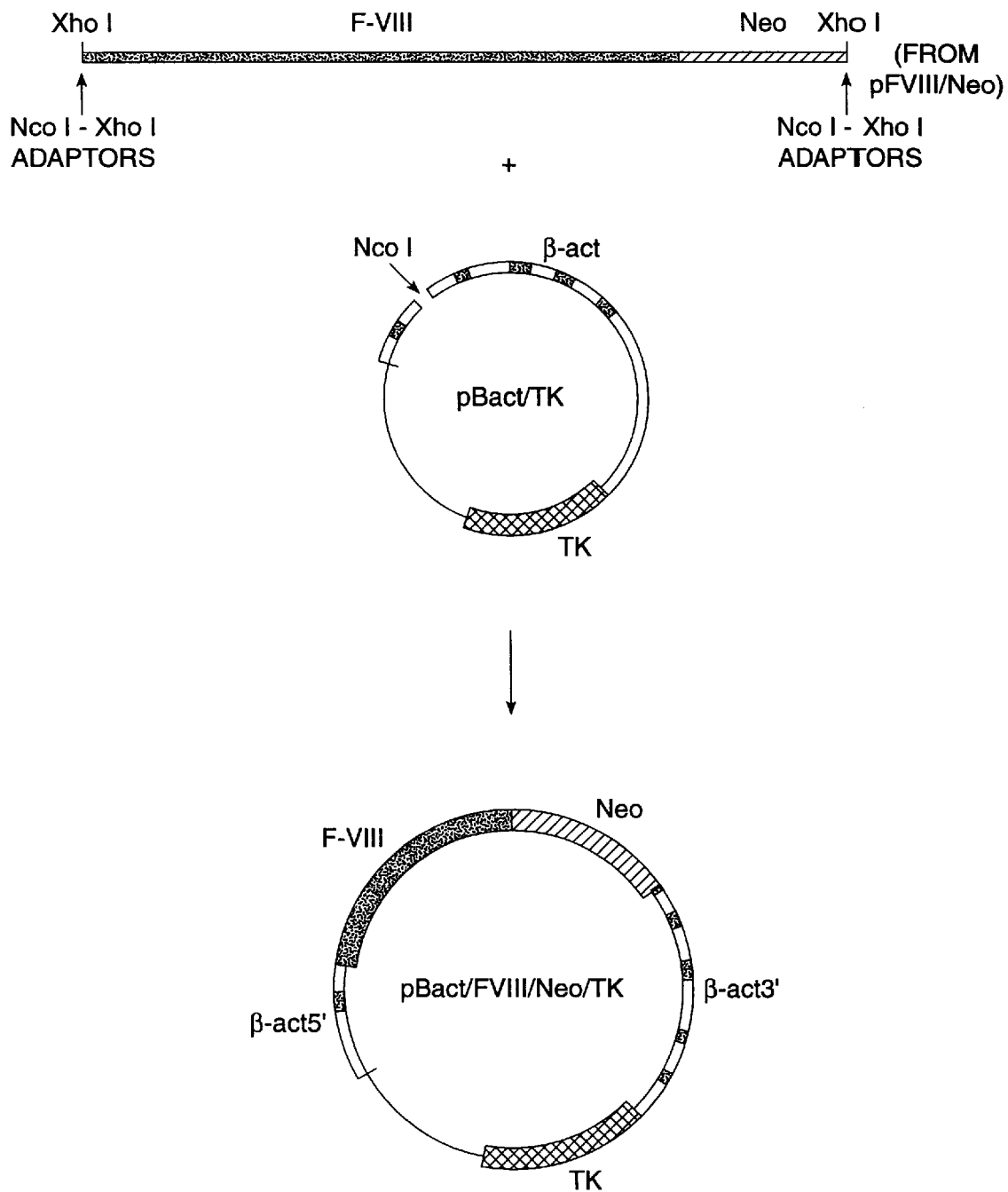

In step 2 (FIG. 7C), the factor VIII/Neo fragment is excised with XhoI as a single piece and inserted using synthetic XhoI/NcoI adaptors at the NcoI site encompassing the met-initiation codon in pBact/TK. This codon lies in the 2nd exon of the β-actin gene, well away from the promoter, such that transcription and splicing of the mRNA is in the normal fashion. The vector so formed is designated pBact/FVIII/Neo/TK.

This vector is digested with either ClaI or HindIII which acts in the polylinker adjacent to the TX gene. The linker vector is then introduced by electroporation into endothelial cells isolated from a hemophiliac patient. The cells are then selected for G418 and gancyclovir resistance. Those cells shown by DNA analysis to contain the factor VIII gene targeted to the β-actin locus or cells shown to express FVIII are then seeded into a vascular graft which is subsequently implanted into the patient's vascular system.

EXAMPLE 5

Replacement of a Mutant PNP Gene in Human Bone Marrow Stem Cells Using PNS

Figure 8:
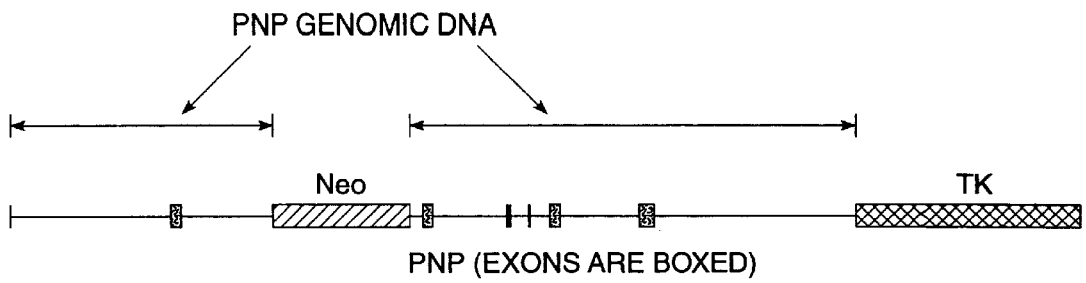
FIG. 8 depicts a PNS vector to correct a defect in the purine nucleoside phosphorylase gene.

The genomic clone of a normal purine nucleoside phosphonylase (PNP) gene, available as a 12.4 kb, Xba-partial fragment (Williams, et al. (1984), *Nucl. Acids Res,* 12, 5779; Williams, et al. (1987), *J. Biol. Chem.* 262, 2332) is inserted at the XbaI site in the vector, pIC-19-R/TK. The neo$^r$ gene from pMcI-Neo is inserted, using synthetic BamHI/XhoI linkers, into the BamHI site in intron 1 of the PNP gene. The linearized version of this vector (cut with ClaI) is illustrated in FIG. 8.

Bone marrow stem cells from PNP patients transfected with this vector are selected for neo$^r$, gan$^r$, in culture, and those cells exhibiting replacement of the mutant gene with the vector gene are transplanted into the patient.

EXAMPLE 6

Inactivation by Insertional Mutagenesis of the Hox 1.1 Locus in Mouse ES Cells, Using a Promoterless PNS Vector A promoterless positive selection marker is obtained using the Neo$^R$ gene, excised at its 5' end by enzyme, EcoRI, from the plasmid, pMCI-Neo. Such a digestion removes the Neo structural gene from its controlling elements.

A promoterless PNS vector is used to insert the Neo gene into the Hox 1/1 gene in ES cells. The Hox 1.1 gene is expressed in cultured embryo cells (Colberg-Poley, et al. (1985), *Nature,* 314, 713) and the site of insertion, the second exon, lies 3' to the promoter of the gene (Kessel, et al. (1987), *PNAS,* 84, 5306; Zimmer, et al. (1989), *Nature,* 338, 150). Expression of Neo will thus be dependent upon insertion at the Hox 1.1 locus.

Vector construction is as follows:

Step 1—The neo gene, missing the transcriptional control sequences is removed from pMCI-Neo, and inserted into the second exon of the 11 kb, FspI-KpnI fragment of Hox 1.1 (Kessel, et al. (1987), supra; Zimmer, et al. (1989), supra).

Figure 9:
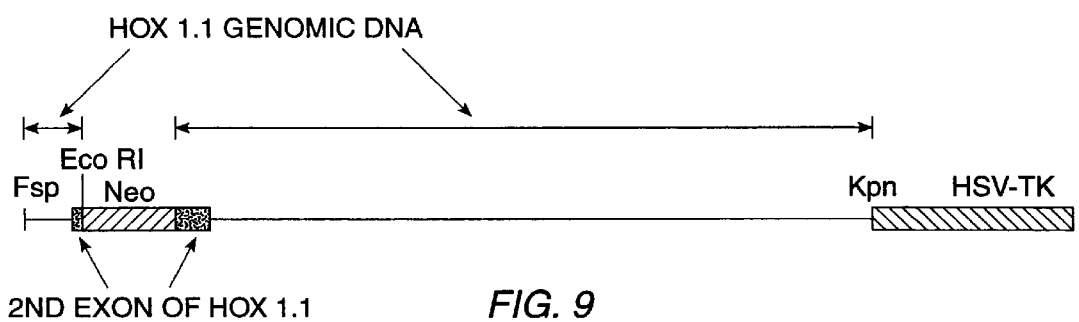
FIG. 9 depicts a vector for promoterless PNS.

Step 2—The Hox 1.1-Neo sequences is then inserted adjacent to the HSV-tk gene is pIC19R/TK, creating the targeting vector, pHox1.1-N/TK. The linearized version of this vector is shown in FIG. 9 This vector is electroporated into ES cells, which are then selected for Neo$^r$, GanC$^r$. The majority of cells surviving this selection are predicted to contain targeted insertions of Neo at the Hox1.1 locus.

EXAMPLE 7

Inducible Promoters

PNS vectors are used to insert novel control elements, for example inducible promoters, into specific genetic loci. This permits the induction of specified proteins under the spatial and/or temporal control of the investigator. In this example, the MT-1 promoter is inserted by PNS into the Int-2 gene in mouse ES cells.

The inducible promoter from the mouse metallothionein-I (MT-I) locus is targeted to the Int-2 locus. Mice generated from ES cells containing this alteration have an Int-2 gene inducible by the presence of heavy metals. The expression of this gene in mammary cells is predicted to result in oncogenesis and provides an opportunity to observe the induction of the disease.

Vector construction is as follows:

Step 1—The EcorI-BglII fragment from the MT-I gene (Palmiter, et al. (1982), Cell, 29, 701) is inserted by blunt-end ligation into the BSSHII site, 5' to the Int-2 structural gene in the plasmid, pAT 153 (see discussion of Example 1).

Step 2—The MCI-Neo gene is inserted into the AvrII site in intron 2 of the Int-2-MT-I construct.

Figure 10:
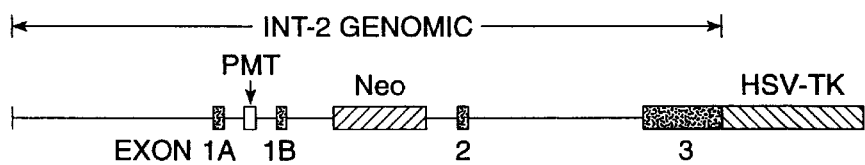
FIG. 10 depicts the construction of a PNS vector to target an inducible promoter into the int-2 locus.

Step 3—The int-2-MT-ILNeo fragment is inserted into the vector, pIC 19R/TK, resulting in the construct shown in FIG. 10.

Introduction of this gene into mouse ES cells by electroporation, followed by Neo$^r$, GanC$^r$, selection results in cells containing the MT-I promoter inserted 5' to the Int-2 gene. These cells are then inserted into mouse blastocysts to generate mice carrying this particular allele.

EXAMPLE 8

Inactivation of the ALS-II Gene in Tobacco Protoplasts by PNS

A number of herbicides function by targeting specific plant metabolic enzymes. Mutant alleles of the genes encoding these enzymes have been identified which confer resistance to specific herbicides. Protoplasts containing these mutant alleles have been isolated in culture and grown to mature plants which retain the resistant phenotype (Botterman, et al. (1988), TIGS, 4, 219; Gasser, et al. (1989), Science, 244, 1293). One problem with this technology is that the enzymes involved are often active in multimer form, and are coded by more than one genetic locus. Thus, plants containing a normal (sensitive) allele at one locus and a resistant allele at another locus produce enzymes with mixed subunits which show unpredictable resistance characteristics.

In this example, the gene product of the ALS genes (acetolactate synthase) is the target for both sulfonylurea and imidazolinone herbicides (Lee, et al. (1987), EMBO, 7, 1241). Protoplasts resistant to these herbicides have been isolated and shown to contain mutations in one of the two ALS loci. A 10 kb SpeI fragment of the ALS-II gene (Lee, et al. (1988), supra; Mazur, et al. (1987), Plant Phys., 85, 1110) is subcloned into the negative selection vector, pIC-19R/TK. A neo$^r$ gene, engineered for expression in plant cells with regulating sequences from the mannopine synthase gene for the TI plasmid is inserted into the EcoRI site in the coding region of the ALS-II. This PNS vector is transferred to the C3 tobacco cell line (Chalef, et al. (1984), Science, 223, 1148), carrying a chlorsulfuronr allele in Als-I.

They are then selected for Neo$^r$, GanC$^r$. Those cells surviving selection are screened by DNA blots for candidates containing insertions in the ALS-IL gene.

Having described the preferred embodiments of the present invention, it will appear to those ordinarily skilled in the art that various modifications may be made to the disclosed embodiments, and that such modifications are intended to be within the scope of the present invention.

What is claimed is:

1. A method of culturing a cell, comprising culturing a cell having a genome comprising a modification of a target DNA sequence, wherein the modification was introduced into the genome of the cell or an ancestor thereof by
   (a) transforming a population of cells with a PNS vector;
   (b) identifying a cell having said genome comprising the modification of the target DNA sequence by selecting for cells containing a positive selection characteristic and against cells containing a negative selection characteristic;
   (c) propagating the cell,
   wherein said PNS vector comprises:
      (1) a first homologous vector DNA sequence capable of homologous recombination with a first region of said target DNA sequence;
      (2) a positive selection marker DNA sequence capable of conferring the positive selection characteristic in said cells;
      (3) a second homologous vector DNA sequence capable of homologous recombination with a second region of said target DNA sequence; and
      (4) a negative selection marker DNA sequence, capable of conferring the negative selection characteristic in said cells, but substantially incapable of homologous recombination with said target DNA sequence;
   wherein the spatial order of said sequences in said PNS vector is: said first homologous vector DNA sequence, said positive selection marker DNA sequence, said second homologous vector DNA sequence and said negative selection marker DNA sequence as shown in FIG. 1;
   wherein the 5'-3' orientation of said first homologous vector sequence relative to said second homologous vector sequence is the same as the 5'-3' orientation of said first region relative to said second region of said target sequence;
   wherein the vector is capable of modifying said target DNA sequence by homologous recombination of said first homologous vector DNA sequence with said first region of said target sequence and of said second homologous vector DNA sequence with said second region of said target sequence.

2. The method of claim 1, wherein the cell is selected from the group consisting of hematopoietic, epithelial, liver, lung, bone marrow, endothelial, mesenchymal, neural and muscle stem cells.

3. The method of claim 2, wherein the cell is a cell of a vertebrate animal.

4. The method claim 3, wherein the cell is a human cell.

5. The method of claim 2, wherein the cell is a bone marrow stem cell.

6. The method of claim 3, wherein the cell is a simian cell.

7. A population of cells comprising:
   (a) first cells having a genome comprising a target sequence modified by insertion of a positive selection marker DNA sequence, wherein said target sequence is the same in each of said first cells and said insertion is effected by homologous recombination of the target sequence with a PNS vector; and
   (b) second cells having genomes modified by insertion of a PNS vector fragment comprising a positive selection marker DNA sequences and a negative selection marker DNA sequence, wherein said PNS vector fragment is randomly distributed in the genomes of said second cells;

wherein said PNS vector comprises:
   (1) a first homologous vector DNA sequence capable of homologous recombination with a first region of said target DNA sequence,
   (2) a positive selection marker DNA sequence capable of conferring a positive selection characteristic in said cells,
   (3) a second homologous vector DNA sequence capable of homologous recombination with a second region of said target DNA sequence;
   (4) a negative selection marker DNA sequence, capable of conferring a negative selection characteristic in said cells, but substantially incapable of homologous recombination with said target DNA sequence;

wherein the spatial order of said sequences in said PNS vector is: said first homologous vector sequence, said positive selection marker DNA sequence, said second homologous vector DNA sequence and said negative selection marker DNA sequence as shown in FIG. 1;

wherein the 5'3' orientation of said first homologous vector sequence relative to said second homologous vector sequence is the same as the 5'3' orientation of said first region relative to said second region of said target sequence;

wherein the vector is capable of modifying said target DNA sequence by homologous recombination of said first homologous vector DNA sequence with said first region of said target sequence and of said second homologous vector DNA sequence with said second region of said target sequence.

* * * * *